US012414930B2

United States Patent
Xu et al.

(10) Patent No.: US 12,414,930 B2
(45) Date of Patent: Sep. 16, 2025

(54) ALL-TRANS RETINOIC ACID LIPOSOME FORMULATION, AND PREPARATION AND USE THEREOF

(71) Applicant: SHANGHAI JIAO TONG UNIVERSITY, Shanghai (CN)

(72) Inventors: Yuhong Xu, Shanghai (CN); Anjie Zheng, Shanghai (CN); Xiaolong Chen, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 875 days.

(21) Appl. No.: 16/615,281

(22) PCT Filed: Aug. 17, 2017

(86) PCT No.: PCT/CN2017/097869
§ 371 (c)(1),
(2) Date: Nov. 20, 2019

(87) PCT Pub. No.: WO2018/033118
PCT Pub. Date: Feb. 22, 2018

(65) Prior Publication Data
US 2021/0283086 A1    Sep. 16, 2021

(30) Foreign Application Priority Data
Aug. 18, 2016 (CN) ......................... 201610686883.5

(51) Int. Cl.
| | |
|---|---|
| *A61K 31/203* | (2006.01) |
| *A61K 9/1272* | (2025.01) |
| *A61K 9/1278* | (2025.01) |
| *A61K 47/10* | (2017.01) |
| *A61K 47/32* | (2006.01) |
| *A61K 47/38* | (2006.01) |
| *A61K 47/40* | (2006.01) |
| *A61P 35/00* | (2006.01) |

(52) U.S. Cl.
CPC .......... *A61K 31/203* (2013.01); *A61K 9/1272* (2013.01); *A61K 9/1278* (2013.01); *A61K 47/10* (2013.01); *A61K 47/32* (2013.01); *A61K 47/38* (2013.01); *A61K 47/40* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,811,119 A | 9/1998 | Mehta et al. | |
| 2002/0058060 A1* | 5/2002 | Kan | A61K 9/1271 424/450 |
| 2005/0214357 A1* | 9/2005 | Wang | A61K 9/127 424/450 |

FOREIGN PATENT DOCUMENTS

CN    10 1843584    9/2010

OTHER PUBLICATIONS

Zheng et al (Preparation of Tretinoin Liposome by Calcium Acetate Gradient Method. China Pharmacy, 17(8): 2006 p. 579-581. (Year: 2006).*
McCormack et al (Entrapment of Cyclodextrin-Drug Complexes into Liposomes: Potential Advantages in Drug Delivery. Journal of Drug Targeting. vol 2, Issue 5 (1994), p. 449-454). (Year: 1994).*
Gubernator (Active methods of drug loading into liposomes: recent strategies for stable drug entrapment and increased in vivo activity, Expert Opinion on Drug Delivery, (2011), 8:5, 565-580) (Year: 2011).*
Clerc (Loading of amphipathic weak acids into liposomes in response to transmembrane calcium acetate gradients. Biochimica et Biophysica Acta 1240 (1995) 257-265) (Year: 1995).*
Aug. 31, 2006, (Aug. 31, 2006), 17(8), ISSN: 1001-0408, pp. 579 to 581. (Zheng Jiayi et al. Preparation of Tretinoin Liposome by Calcium Acetate Gradient Method. China Pharmacy.).
Jan. 31, 2016, (Jan. 31, 2016), 32(2), ISSN: 1006-5725, and pp. 178-180. (Chu Mei et al. All-transretinoicacidreduces myeloid-derived suppressor cells in tongue carcinoma mice. The Journal of Practical Medicine.).
Charoensit, P. et al., "Enhanced growth inhibition of metastatic lung tumors by intravenous injection of ATRA-cationic liposome/IL-12 pDNA complexes in mice", 2010, vol. 17, pp. 512-522.
Li, R.J. et al., "All-trans retinoic acid stealth liposomes prevent the relapse of breast cancer arising from the cancer stem cells", Journal of Controlled Release, 2011, vol. 149, pp. 281-291.

* cited by examiner

*Primary Examiner* — Jake M Vu
(74) *Attorney, Agent, or Firm* — ArentFox Schiff LLP; Shawn P. Foley; Chris Lorenc

(57) ABSTRACT

The present disclosure relates to an all-trans retinoic acid liposome formulation and a preparation method thereof. The all-trans retinoic acid liposome formulation includes all-trans retinoic acid and a liposome vector. The disclosure adopts an active drug loading method, including a calcium acetate gradient method or a sodium acetate gradient method. The prepared all-trans retinoic acid formulation has high drug loading and high stability in vivo, thereby increasing the blood concentration and prolonging the half-life of the all-trans retinoic acid.

11 Claims, 12 Drawing Sheets

ALL-TRANS RETINOIC ACID LIPOSOME FORMULATION, AND PREPARATION AND USE THEREOF

CROSS REFERENCE TO RELATED PATENT APPLICATION

The present application is the US national stage of PCT/CN2017/097869 filed on Aug. 17, 2017, which claims the priority of the Chinese patent applications No. 201610686883.5 filed on Aug. 18, 2016, which applications are incorporated herein by reference.

BACKGROUND OF THE PRESENT DISCLOSURE

Field of Disclosure

The present disclosure relates to the field of biotechnology, specifically to all-trans retinoic acid liposome formulation, and preparation and use thereof.

DESCRIPTION OF RELATED ARTS

Retinoic acid is a metabolite of vitamin A in the body. All-trans retinoic acid (ATRA) is used as a drug to treat acne, and is also an important drug for the clinical treatment of acute promyelocytic leukemia (APL). All-trans retinoic acid (ATRA) affects gene expression by binding to specific receptors (RARs, RXRs and RORs) in cells, and promotes APL cell differentiation and PML/RARα gene in the treatment of acute promyelocytic leukemia degradation, to achieve the effect of treatment.

However, the clinical application of all-trans retinoic acid drugs is limited by the following aspects: 1 all-trans retinoic acid has very low water solubility (4.77e-03 g/l); 2 all-trans retinoic acid plasma half-life is more short, and its efficacy requires maintaining a certain blood concentration over a long period of time, and the concentration of the drug in the target organ. Therefore, it is particularly important to choose a drug delivery method suitable for all-trans retinoic acid.

Liposomes have been used as a nano drug delivery vehicle for more than 30 years. A variety of anticancer drugs based on liposome delivery systems have been widely used in clinical treatment of tumors. The most successful drug is doxorubicin liposome. The advantage of liposome as a drug delivery system is that it changes the biodistribution of the drug, reduces the systemic toxicity of the drug, and can achieve a long circulation/targeting effect by specific modification on the liposome, thus increasing the drug concentration of the target tissue.

Most of the previously reported all-trans retinoic acid liposome formulations incorporate all-trans retinoic acid into the phospholipid bilayer. Due to the physical properties of all-trans retinoic acid, the all-trans retinoic acid liposome produced by this method is not ideal in terms of drug loading and stability in vivo.

SUMMARY OF THE PRESENT DISCLOSURE

In order to overcome the problems in the prior art, it is an object of the present disclosure to provide an all-trans retinoic acid formulation and its preparation and use.

In order to achieve the above and other related objects, the present disclosure adopts the following technical solutions:

In a first aspect of the present disclosure, it provides an all-trans retinoic acid liposome formulation comprising all-trans retinoic acid and a liposome vector.

Preferably, the all-trans retinoic acid liposome formulation further comprises a solubilizing molecule for increasing a solubility of the all-trans retinoic acid.

Further preferably, the solubilizing molecule is selected from any one or a combination of PVP, HPMC, cyclodextrin, and PEG.

Further preferably, a molar ratio of the solubilizing molecule to the all-trans retinoic acid is in a range of (38-0.075):1.

In a preferred embodiment of the present disclosure, the cyclodextrin is selected from hydroxypropyl-β-cyclodextrin, sulfobutyl-β-cyclodextrin or methyl-β-cyclodextrin.

In a preferred embodiment of the disclosure, the PEG is selected from PEG-400.

When cyclodextrin is selected as the solubilizing molecule, the molar ratio of the solubilizing molecule to the all-trans retinoic acid may be in a range of (20-2):1.

When PVP is selected as the solubilizing molecule, the molar ratio of the solubilizing molecule to the all-trans retinoic acid may be in a range of (1.5-0.075):1.

When PEG-400 is selected as the solvating molecule, the molar ratio of the solubilizing molecule to the all-trans retinoic acid may be in a range of (38-9.5):1.

Preferably, the molar ratio of the all-trans retinoic acid to the liposome vector is in a range of 1: (5-20).

Preferably, the raw material of the liposome comprises a phospholipid, cholesterol and a pegylated phospholipid.

Further preferably, the molar ratio between the phospholipid, the cholesterol and the pegylated phospholipid in the raw material of the liposome is in a range of (30-80): (0.1-40): (0.1-30).

Further preferably, the raw material of the liposome comprises HSPC, CHOL and DSPE-PEG.

Further preferably, the molar ratio between the HSPC, CHOL, and DSPE-PEG in the raw material of the liposome is in a range of (30-80): (0.1-40): (0.1-30). More preferably, the molar ratio between the HSPC, CHOL, and DSPE-PEG in the raw material of the liposome is 57:38:5.

Preferably, the molecular weight of PEG in the DSPE-PEG ranges from 50 to 10,000. More preferably, the molecular weight of PEG in the DSPE-PEG is 2000.

Preferably, the liposome is a single compartment liposome.

Preferably, the liposome has a particle diameter ranging from 30 nm to 200 nm. More preferably, the liposome has a particle diameter ranging from 50 to 150 nm. More preferably, the liposome has a particle diameter of 70 nm to 130 nm.

Preferably, the liposome has a narrow particle diameter distribution, and D95 of the liposome (having a particle diameter smaller than 95% of the total amount of the liposome) is 120 nm or less. More preferably, D95 is 110 nm or less, and more preferably, D95 is 95 nm or less.

Preferably, in the all-trans retinoic acid liposome formulation, the concentration of the all-trans retinoic acid is 0.1 mg/ml or more. Further preferably, in the all-trans retinoic acid liposome formulation, the concentration of the all-trans retinoic acid is 0.5 mg/ml or more. More preferably, in the all-trans retinoic acid liposome formulation, the concentration of the all-trans retinoic acid ranges from 0.5 to 5 mg/ml.

Preferably, the all-trans retinoic acid liposome formulation is an injectable administration formulation.

Further preferably, the injectable administration formulation is selected from a subcutaneous injection form, an intravenous injection form, an intramuscular injection form, or a pelvic injection form.

In a second aspect of the disclosure, it provides a method of preparing an all-trans retinoic acid liposome formulation, which is an active drug loading method.

Preferably, the preparation method is a calcium acetate gradient method. Alternatively, the method is a sodium acetate gradient method.

Further preferably, the calcium acetate gradient method comprises the operations of:
(1) taking all raw materials for preparing a liposome according to a ratio, and dissolving with ethanol to obtain an ethanol mixture;
(2) adding an aqueous solution of calcium acetate having a pH of 7.0 to 11.0 to the ethanol mixture in operation (1) to obtain a liposome vesicle;
(3) sequentially extruding the liposome vesicle obtained in operation (2) through polycarbonate membranes having different pore diameters to obtain a a blank liposome having a uniform particle diameter;
(4) the inner and outer aqueous phases of the blank liposome prepared in operation (3) are all aqueous solutions of calcium acetate, placing the blank liposome into an isotonic liquid having a pH of 6.0 to 7.0, to obtain a blank liposome having a calcium acetate gradient between an inner aqueous phase and an outer aqueous phase;
(5) adding an all-trans retinoic acid suspension to the blank liposome having the calcium acetate gradient between the inner aqueous phase and the outer aqueous phase obtained in operation (4), incubating, and removing free all-trans retinoic acid, to obtain the all-trans retinoic acid liposome formulation.

Preferably, in operation (2), the concentration of calcium acetate in the aqueous solution of calcium acetate is 120 mM to 360 mM.

Preferably, when the all-trans retinoic acid liposome formulation contains a solubilizing molecule, in operation (2), aqueous solution of calcium acetate contains a solubilizing molecule.

Preferably, a calcium acetate gradient is provided between the inner aqueous phase and the outer aqueous phase of the liposome obtained in operation (4).

Preferably, the inner aqueous phase of the liposome obtained in operation (4) is an aqueous solution of calcium acetate having a pH of 7.0 to 11.0, and the outer aqueous phase is an isotonic solution having a pH of 6.0 to 7.0.

Further preferably, the isotonic solution is selected from a group consisting of HEPEs buffer solution containing 0.9% NaCl or 10% sucrose at a concentration of 10 mM.

In addition, the sodium acetate gradient method comprises the operations of:
(1) taking all raw materials for preparing a liposome according to a ratio, and dissolving with ethanol to obtain an ethanol mixture;
(2) adding an aqueous solution of sodium acetate having a pH of 7.0 to 11.0 to the ethanol mixture in operation (1) to obtain a liposome vesicle;
(3) sequentially extruding the liposome vesicle obtained in operation (2) through polycarbonate membranes having different pore diameters to obtain a blank liposome having a uniform particle diameter;
(4) the inner and outer aqueous phases of the blank liposome prepared in operation (3) are all aqueous solutions of sodium acetate, placing the blank liposome into an isotonic liquid having a pH of 6.0 to 7.0, to obtain a blank liposome having a sodium acetate gradient between an inner aqueous phase and an outer aqueous phase.
(5) adding an all-trans retinoic acid suspension to the blank liposome having the sodium acetate gradient between the inner aqueous phase and the outer aqueous phase obtained in operation (4), incubating, and removing free all-trans retinoic acid, to obtain the all-trans retinoic acid liposome formulation.

Preferably, in operation (2), the concentration of calcium acetate in the aqueous solution of sodium acetate is 120 mM to 360 mM.

Preferably, when the all-trans retinoic acid liposome formulation contains a solubilizing molecule, in operation (2), the aqueous solution of sodium acetate contains a solubilizing molecule.

Preferably, a sodium acetate gradient is provided between the inner aqueous phase and the outer aqueous phase of the liposome obtained in operation (4).

Preferably, the inner aqueous phase of the liposome obtained in operation (4) is an aqueous solution of calcium acetate having a pH of 7.0 to 11.0, and the outer aqueous phase is an isotonic solution having a pH of 6.0 to 7.0.

Further preferably, the isotonic solution is selected from a group consisting of HEPEs buffer solution containing 0.9% NaCl or 10% sucrose at a concentration of 10 mM.

The method disclosed by the present disclosure can be used to increase the solubility or drug concentration of all-trans retinoic acid in all-trans retinoic acid liposome formulations.

Furthermore, the method can be used to increase the effect of all-trans retinoic acid on tumor-associated macrophages in all-trans retinoic acid liposome formulations.

In addition, the method can be used to enhance the effect of all-trans retinoic acid on myeloid suppressor cells in all-trans retinoic acid liposome formulations.

In a third aspect of the disclosure, it provides the use of the above-mentioned all-trans retinoic formulation for the preparation of a medicament for treating tumor.

Preferably, the medicament for the treatment of tumor is a drug for abnormal myeloid suppressor cells, inducing differentiation of myeloid suppressor cells, and inhibiting tumor proliferation and recurrence in patients with tumor.

Further preferably, the myeloid suppressor cells are myeloid suppressor cells of breast cancer, colon cancer, ovarian cancer, lung cancer, kidney cancer, stomach cancer, liver cancer, cervical cancer, endometrial cancer, bladder cancer, prostate cancer, pancreatic cancer, colorectal cancer, basal cell carcinoma, melanoma, follicular lymphoma or small lymphocytoma.

The disclosure also provides the use of all-trans retinoic acid or the above-mentioned all-trans retinoic acid in the preparation of a medicament, the use is selected from any one or more of the following:
(1) promoting the differentiation of MDSCs into mature DCs in a tumor site;
(2) promoting the proliferation of T cells in the tumor site;
(3) reducing the number of CD33*HLA-DR-MDSC in tumor infiltrating myeloid-derived cells;
(4) reducing the number of MDSCs in the tumor site.

Further, the use is selected from any one or more of the following:
(1) promoting the differentiation of MDSCs at a tumor site into mature DCs;
(2) promoting the proliferation of T cells in head and neck mucosal squamous cell carcinoma PBMC;

(3) reducing the number of CD33'HLA-DR-MDSC in tumor infiltrating myeloid-derived cells of bladder cancer;

(4) reducing the number of MDSCs at the tumor site.

In the fourth aspect of the present disclosure, it provides a method for treating tumor, comprising the operation of: administering the all-trans retinoic acid formulation described above to a patient. The particular dosage of administration will be within the scope well known by those skilled in the art.

The present disclosure has the following beneficial effects compared with the prior art:

(1) The present disclosure is the first application of an active drug loading method to load all-trans retinoic acid to form an all-trans retinoic acid liposome preparation having a high drug loading amount and stable in vivo.

According to the disclosure, the all-trans retinoic acid drug is embedded in a liposome phospholipid bilayer membrane or bound to a liposome phospholipid bilayer membrane or encapsulated in a liposome capsule. The all-trans retinoic acid drug is embedded in the liposome phospholipid bilayer membrane, meaning that the all-trans retinoic acid is partially or completely encapsulated in the hydrophobic layer of the phospholipid bilayer membrane by hydrophobic action; the all-trans dimension The combination of formic acid on the liposome phospholipid bilayer membrane means that the all-trans retinoic acid is bound to the liposome phospholipid bilayer membrane by interaction with a phospholipid bilayer through charge, hydrophobic, physical or chemical adsorption; The all-trans retinoic acid drug is encapsulated in the liposome capsule. It refers to all-trans retinoic acid in the form of a soluble or all-trans retinoic acid mono- or all-trans-metamate precipitate. The layer is encapsulated in a liposome capsule.

(2) It has been found through long-term experiments that the all-trans retinoic acid lipid prepared by the present disclosure has higher drug loading and better in vivo stability than other types of all-trans retinoic acid lipid. Furthermore, the all-trans retinoic acid lipid prepared by the present disclosure has a solubility of all-trans retinoic acid from 0.01 mg/ml in the prior art, and is increased by at least 0.1 mg/ml or more, at least 100 times.

DETAILED DESCRIPTION

Figure 1A:
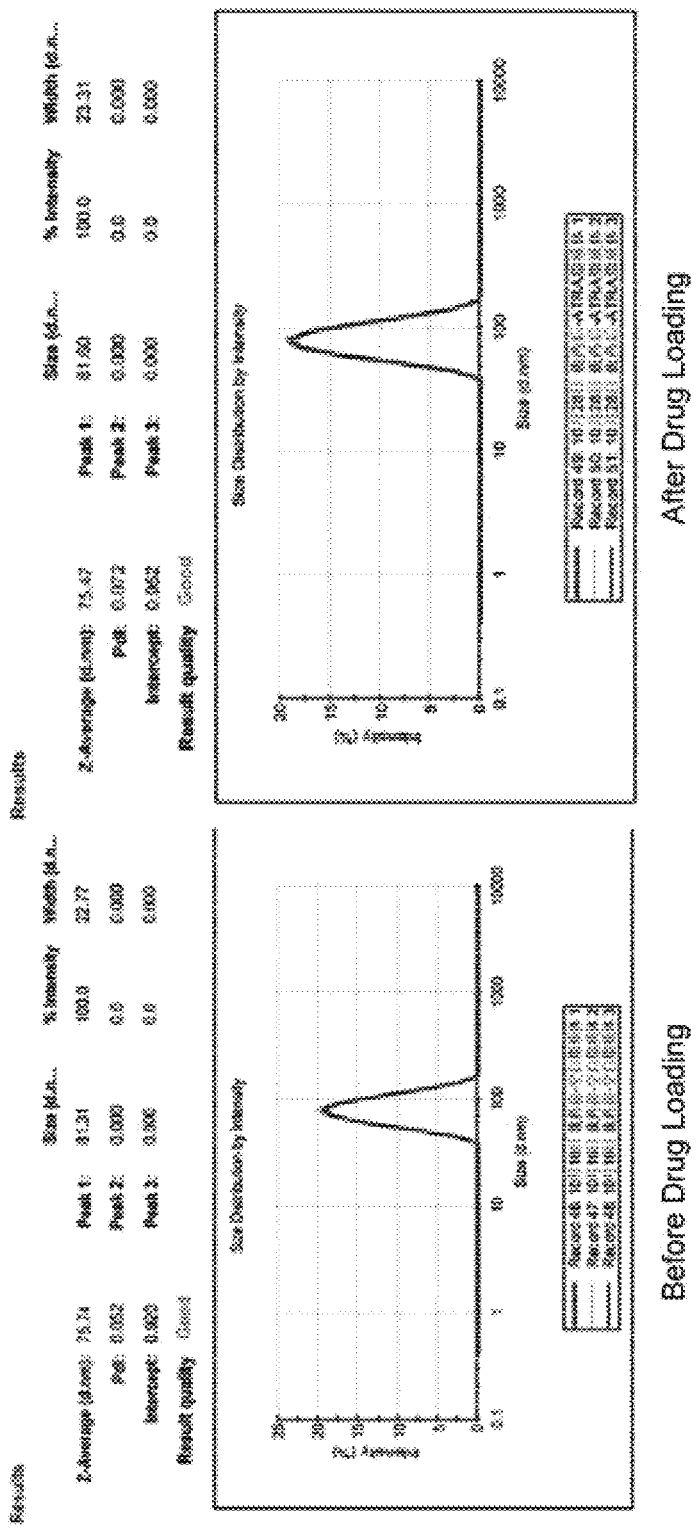
FIG. 1A shows the particle size of liposomes before and after drug loading of Formula 1.

Before the present disclosure is further described, it should be understood that the protection scope of the present disclosure is not limited to the specific embodiments described below; it should also be understood that the terms used in the embodiments of the present disclosure are intended to describe the specific embodiments, and not to limit the protection scope of the present disclosure. The test methods which do not specify the specific conditions in the following examples are usually carried out according to conventional conditions or according to the conditions recommended by each manufacturer.

When the numerical values are given by the examples, it should be understood that the two endpoints of each numerical range and any one of the two endpoints may be selected, unless otherwise described in the present disclosure. All technical and scientific terms used in the present disclosure have the same meaning as commonly understood by those skilled in the art, unless otherwise defined. In addition to the specific methods, devices, and materials used in the embodiments, any method, device, and material in the prior art that are similar to or equal to that described in the embodiments of the present disclosure may also be used to implement the present disclosure according to the prior art mastered by those skilled in the art and the description of the present disclosure.

Unless otherwise stated, the experimental methods, detection methods, and preparation methods disclosed in the present disclosure all adopt conventional molecular biology, biochemistry, chromatin structure and analysis, analytical chemistry, cell culture, and recombinant DNA technology in the art and conventional technology in related fields. These techniques are well described in the prior literature, for specific detail, referring to Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, and the like.

Example 1 Preparation and Identification of All-trans Retinoic Acid Liposomes

Hydrogenated soybean phosphatide (HSPC) was purchased from NOF Corporation, pegylated phospholipid: distearoylphosphatidylethanolamine-polyethylene glycol 2000 (DSPE-PEG2000), and cholesterol were purchased from Avanti Polar Lipids; All-trans retinoic acid was purchased from Sigma.

1. Preparation of All-trans Retinoic Acid Liposomes (a) Preparation of Formula 1

(1) 121.742 mg of HSPC (molecular weight: 783.8), 38.22 mg of DSPE-PEG2000, and 40.04 mg of cholesterol were weighed and dissolved in 1.6 mL of ethanol, and water bathed to be dissolved and mixed at 70° C. in a water bath to obtain an ethanol mixture.

(2) The obtained ethanol mixture from operation (1) was then added with 6.4 mL calcium acetate buffer (PH 9.0, which consisted of 200 mM calcium acetate and water), and water bathed at 70° C. for 30 minutes to obtain liposome vesicles.

(3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 90 nm and an aqueous phase of calcium acetate.

(4) The liposome prepared in operation (3) was dialyzed through a dialysis membrane with a 10000 MWCO (Molecular Weight Cut off) in a 10% sucrose aqueous solution (pH 6~7), and the outer aqueous phase of the liposome was replaced with a 10% sucrose aqueous solution (pH 6~7) to obtain a calcium acetate liposome having a phospholipid bilayer membrane, and the inner aqueous phase and outer aqueous phase of the bilayer membrane have a certain pH gradient and an ion gradient. Specifically, the inner aqueous phase of the bilayer membrane was an aqueous solution of calcium acetate (pH 9.0, concentration: 200 mM), and the outer aqueous phase of the bilayer membrane was a sucrose aqueous solution (pH 6~7, mass fraction of 10%).

(5) 4 mg/mL suspension of all-trans retinoic acid was added to the calcium acetate liposome obtained from operation (4), the volume ratio of the added suspension of all-trans retinoic acid to the calcium acetate liposome was 1:1, and the mixture was incubated for 45 minutes at 60° C. After incubation, the free all-trans retinoic acid not loading into the liposome was removed by the dialysis membrane with a 10000 MWCO, and the final all-trans retinoic acid liposome was obtained, which was labeled as Formula 1.

(b) Preparation of Formula 2

When the molar ratio of the all-trans retinoic acid to the liposome vector was 1:5, the all-trans retinoic acid liposome was prepared by using the above-mentioned method, the method was modified as follows:

When the molar ratio of the all-trans retinoic acid to the liposome vector was 1:5, operation (1) was modified as follows:

60.87092 mg of HSPC (molecular weight: 783.8), 19.1994 mg of DSPE-PEG2000, and 20.01967 mg of cholesterol were weighed and dissolved in 1.6 mL of ethanol, and water bathed to be dissolved and mixed at 70° C. in a water bath to obtain an ethanol mixture.

The all-trans retinoic acid liposome obtained by the blank liposome prepared under this condition and 8.175 mg of all-trans retinoic acid was labeled as Formula 2.

(c) Preparation of Formula 3

When the molar ratio of the all-trans retinoic acid to the liposome vector was 1:20, the all-trans retinoic acid liposome was prepared by using the above-mentioned method, the method was modified as follows:

When the molar ratio of the all-trans retinoic acid to the liposome vector was 1:20, operation (1) was modified as follows:

243.48369 mg of HSPC (molecular weight: 783.8), 76.43760 mg of DSPE-PEG2000, and 80.07870 mg of cholesterol were weighed and dissolved in 1.6 mL of ethanol, and water bathed to be dissolved and mixed at 70° C. in a water bath to obtain an ethanol mixture.

The all-trans retinoic acid liposome obtained by the blank liposome prepared under this condition and 8.175 mg of all-trans retinoic acid was labeled as Formula 3.

(d) Preparation of Formula 4

When the molar ratio of all-trans retinoic acid to liposome vector was 0.08, all-trans retinoic acid liposomes were prepared as described above and labeled as Formula 4.

(e) Preparation of Formula 5

When the molar ratio of all-trans retinoic acid to liposome vector was 0.12, all-trans retinoic acid liposomes were prepared as described above and labeled as Formula 5.

(1) 0.097 g of HSPC (molecular weight: 783.8), 0.031 g of DSPE-PEG2000, and 0.031 g of cholesterol were weighed and dissolved in 1.6 mL of ethanol, and water bathed to be dissolved and mixed at 70° C. in a water bath to obtain an ethanol mixture.

(2) The obtained ethanol mixture from operation (1) was then added with 6.4 mL calcium acetate buffer (PH 9.0, which consisted of 200 mM calcium acetate and water), and water bathed at 70° C. for 30 minutes to obtain liposome vesicles.

(3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 90 nm and an aqueous phase of calcium acetate.

(4) The liposome prepared in operation (3) was dialyzed through a 0.2 μm of sterile filtration membrane in a 10% sucrose aqueous solution (pH 7), to obtain a calcium acetate liposome having a phospholipid membrane, and the inner aqueous phase and outer aqueous phase of the phospholipid membrane have a certain pH gradient and an ion gradient. Specifically, the inner aqueous phase of the bilayer membrane was an aqueous solution of calcium acetate (pH 9.0, concentration: 200 mM), and the outer aqueous phase of the bilayer membrane was a sucrose aqueous solution (mass fraction of 10%).

(5) 20 mg/mL suspension of all-trans retinoic acid was added to the calcium acetate liposome obtained from operation (4), the mixture was incubated for 45 minutes at 60° C., and the final all-trans retinoic acid liposome was obtained.

(f) Preparation of Formula 6

When the molar ratio of all-trans retinoic acid to liposome vector was 0.2, all-trans retinoic acid liposomes were prepared by the following operations:

(1) 243.484 mg of HSPC (molecular weight: 783.8), 76.44 mg of DSPE-PEG2000, and 80.08 mg of cholesterol were weighed and dissolved in 1 mL of ethanol, and water bathed to be dissolved and mixed at 70° C. in a water bath to obtain an ethanol mixture.

(2) The obtained ethanol mixture from operation (1) was then added with 5 mL calcium acetate buffer (PH 9.0, which consisted of 200 mM calcium acetate and water), and water bathed at 70° C. for 30 minutes to obtain liposome vesicles.

(3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 80 nm and an aqueous phase of calcium acetate.

(4) The liposome prepared in operation (3) was dialyzed through a dialysis membrane with a 10000 MWCO (Molecular Weight Cut off) in a 10% sucrose aqueous solution (pH 6~7), and the outer aqueous phase of the liposome was replaced with a 10% sucrose aqueous solution (pH 6~7) to obtain a calcium acetate liposome having a phospholipid bilayer membrane, and the inner aqueous phase and outer aqueous phase of the bilayer membrane have a certain pH gradient and an ion gradient. Specifically, the inner aqueous phase of the bilayer membrane was an aqueous solution of calcium acetate (pH 9.0, concentration: 200 mM), and the outer aqueous phase of the bilayer membrane was a sucrose aqueous solution (pH 6~7, mass fraction of 10%).

(5) 3.3 mg/mL suspension of all-trans retinoic acid was added to the calcium acetate liposome obtained from operation (4), the volume ratio of the added suspension of all-trans retinoic acid to the calcium acetate liposome was 1:1, and the mixture was incubated for 45 minutes at 60° C. After incubation, the free all-trans retinoic acid not loading into the liposome was removed by the dialysis membrane with a 10000 MWCO, and the final all-trans retinoic acid liposome was obtained, which was labeled as Formula 6.

2. Characterization of the All-trans Retinoic Acid Liposome (a) Identification of Encapsulation Efficiency of the All-trans Retinoic Acid Liposome The purified all-trans retinoic liposome formulation was destroyed with 9 volumes of methanol, and the encapsulation efficiency was determined by high performance liquid chromatography of a UV detector. Measurement conditions: ODS column (Diamonsil, 5 μm, 250×4.6 mm); detection temperature was 25° C.; detection wavelength was 340 nm; flow rate was 1.0 ml/min; mobile phase of triethylamine hydrochloride buffer (pH=4)/acetonitrile/methanol (volume ratio was 17.5:57.5:25). The encapsulation efficiency (EE) of all-trans retinoic acid was calculated according to the following formula: $EE=(W_i/W_{total})\times100\%$, wherein $W_i$ is the mass of the all-trans retinoic acid in the liposome formulation which is destroyed by methanol after purification. $W_{total}$ is the mass of the all-trans retinoic acid before dialysis and separation of free drug, which has the same volume as the all-trans retinoic acid after dialysis. The results showed that the encapsulation efficiency of ATRA loading into liposome with Formula 1 was about 80%, the encapsulation efficiency of ATRA loading into liposome with Formula 2 was about 90%, the encapsulation efficiency of ATRA loading into liposome with Formula 3 was about 95%, the encapsulation efficiency of ATRA loading into liposome with Formula 4 was about 92%, the encapsulation efficiency of ATRA loading into liposome with Formula 5 was about 93%, and the encapsulation efficiency of ATRA loading into liposome with Formula 6 was about 95%.

(b) Particle Size of the All-trans Retinoic Acid Liposome

The particle size experiment of the all-trans retinoic liposome formulation was repeated three times to obtain the average value±standard deviation.

As a result, as shown in FIG. 1A, the average particle size of the Formula 1 was about 70 nm with the particle size distribution (PDI)<0.3.

The average particle size of the Formula 2 was about 75 nm with the particle size distribution (PDI)<0.3.

The average particle size of the Formula 3 was about 75 nm with the particle size distribution (PDI)<0.3.

The average particle size of the Formula 4 was about 70 nm with the particle size distribution (PDI)<0.3.

The average particle size of the Formula 5 was about 70 nm with the particle size distribution (PDI)<0.3.

Figure 1B:
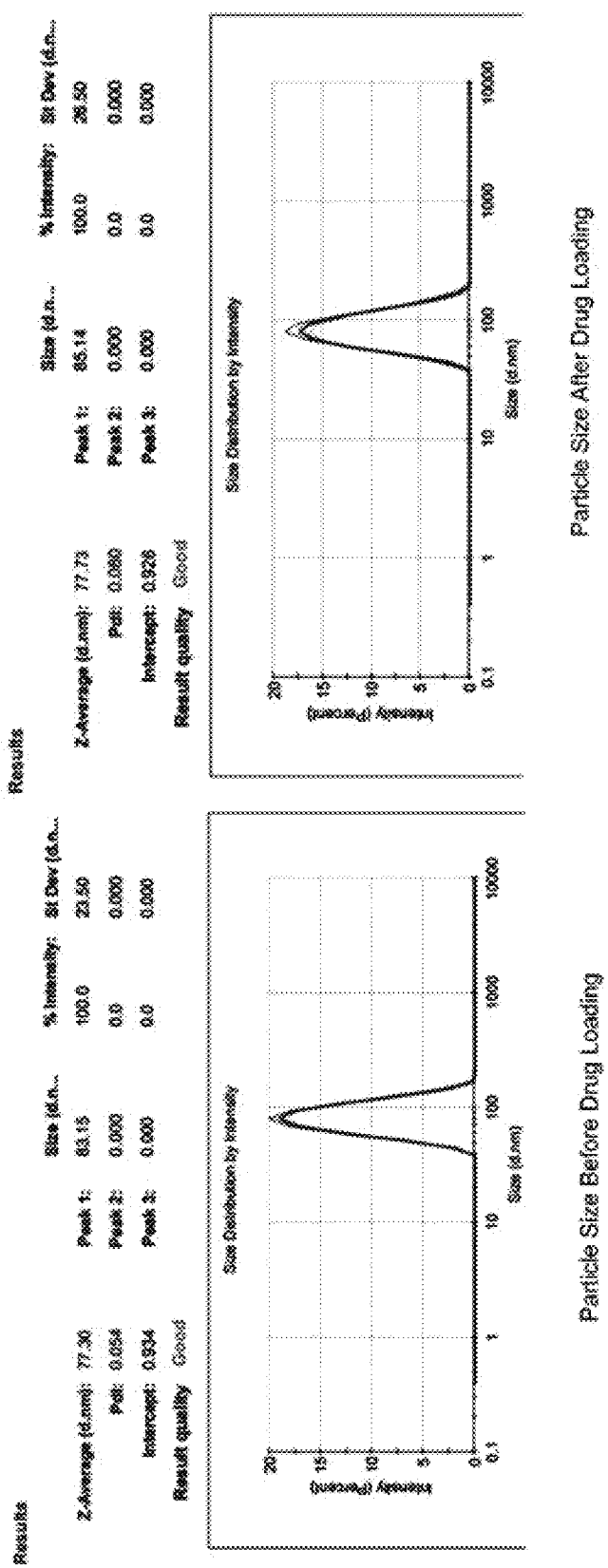
FIG. 1B shows the particle size of liposomes before and after drug loading of Formula 6.

As shown in FIG. 1B, the average particle size of the Formula 6 was about 70 nm with the particle size distribution (PDI)<0.3.

Example 2 Comparison of Active Drug-loading Method and Passive Drug-loading Method for Preparing the All-trans Retinoic Acid Liposome 1. Active Drug-loading Method and Passive Drug-loading Method for Preparing the All-trans Retinoic Acid Liposome (1) 121.742 mg of HSPC (molecular weight: 783.8), 38.22 mg of DSPE-PEG2000, and 40.04 mg of cholesterol were weighed and dissolved in 1.6 mL of ethanol, and water bathed to be dissolved and mixed at 70° C. in a water bath to obtain an ethanol mixture.

(2) The obtained ethanol mixture from operation (1) was then added with 2.5 mL calcium acetate buffer (PH 9.0, which consisted of 200 mM calcium acetate and water), and water bathed at 70° C. for 30 minutes to obtain liposome vesicles.

(3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 80 nm and an aqueous phase of calcium acetate.

(4) The liposome prepared in operation (3) was dialyzed through a dialysis membrane with a 10000 MWCO (Molecular Weight Cut off) in a 10% sucrose aqueous solution (pH 6~7), to obtain a calcium acetate liposome having a phospholipid bilayer membrane, and the inner aqueous phase and outer aqueous phase of the bilayer membrane have a certain pH gradient and an ion gradient.

(5) 4 mg/mL suspension of all-trans retinoic acid was added to the calcium acetate liposome obtained from operation (4), the volume ratio of the added suspension of all-trans retinoic acid to the calcium acetate liposome was 1:1, and the mixture was incubated for 45 minutes at 60° C. After incubation, the free all-trans retinoic acid not loading into the liposome was removed by the dialysis membrane with a 10000 MWCO, and the final all-trans retinoic acid liposome was obtained.

2. Passive Drug-loading Method for Preparing the All-trans Retinoic Acid Liposome
   (1) 121.742 mg of HSPC (molecular weight: 783.8), 38.22 mg of DSPE-PEG2000, and 40.04 mg of cholesterol were weighed and dissolved in 1.6 mL of ethanol, and water bathed to be dissolved and mixed at 70° C. in a water bath to obtain an ethanol mixture.
   (2) The obtained ethanol mixture from operation (1) was then added with 2.5 mL calcium acetate buffer, and water bathed at 70° C. for 30 minutes to obtain liposome vesicles.
   (3) The liposome vesicles obtained from operation (2) were sequentially extruded through polycarbonate membranes having 400 nm, 200 nm, 100 nm, and 50 nm pores for 8 times respectively, to finally obtain liposomes having an average particle diameter of about 90 nm and an aqueous phase of non-calcium acetate.
   (4) 4 mg/mL suspension of all-trans retinoic acid was added to the calcium acetate liposome obtained from operation (3), the volume ratio of the added suspension of all-trans retinoic acid to the calcium acetate liposome was 1:1, and the mixture was incubated for 45 minutes at 60° C. After incubation, the free all-trans retinoic acid not loading into the liposome was removed by the dialysis membrane with a 10000 MWCO, and the final all-trans retinoic acid liposome was obtained.

Figure 2:
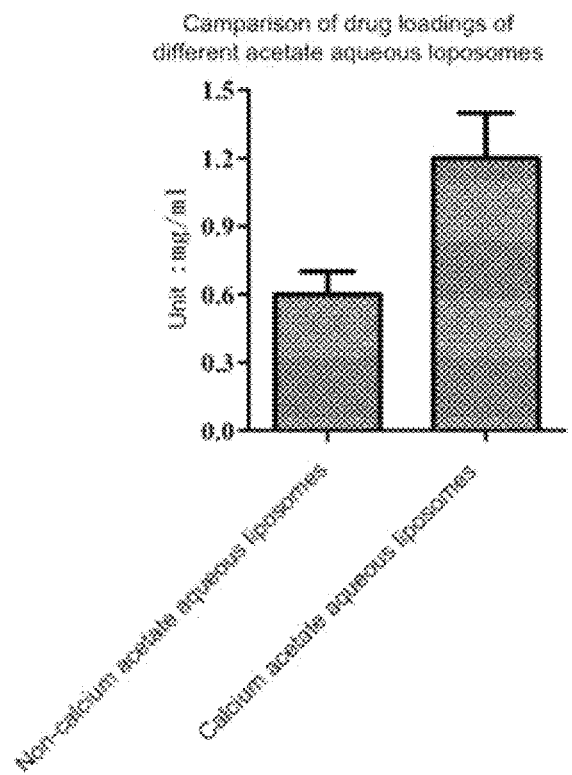
FIG. 2 shows the final drug loadings achieved after removal of free drug by calcium acetate aqueous liposomes and non-calcium acetate aqueous liposomes.

3. Comparison of Loading Dosage by Active/Passive Loading Method for Drug Loading The purified all-trans retinoic liposome formulation was destroyed with 9 volumes of methanol, and the encapsulation efficiency was determined by high performance liquid chromatography of a UV detector. Measurement conditions: ODS column (Diamonsil, 5 μm, 250×4.6 mm); detection temperature was 25° C.; detection wavelength was 340 nm; flow rate was 1.0 ml/min; mobile phase of triethylamine hydrochloride buffer (pH=4)/acetonitrile/methanol (volume ratio was 17.5:57.5:25). The encapsulation efficiency (EE) of all-trans retinoic acid was calculated according to the following formula: EE=(Wi/Wtotal)×100%, wherein Wi is the mass of the all-trans retinoic acid in the liposome formulation which is destroyed by methanol after purification. Wtotal is the mass of the all-trans retinoic acid before dialysis and separation of free drug, which has the same volume as the all-trans retinoic acid after dialysis. The result was shown in FIG. 2, the dosage of active loading method and passive loading method were 1.2 mg/mL and 0.6 mg/mL respectively.

It can be seen that comparing the drug loading efficiency of the liposome prepared under different aqueous conditions, after the removal of the free drug, the all-trans retinoic acid liposome obtained finally has a significant difference in drug loading. The results indicate that calcium acetate aqueous phase liposomes have significant advantages in drug loading.

4. Comparison of Cumulative Release of Active Drug Loading Method and Passive Drug Loading Method in Vitro
   (1) Preparing PBS dialysate containing 10% serum.
   (2) 400 μl of all-trans retinoic acid liposomes prepared by the two different methods mentioned above were loaded into different dialysis tube (using a dialysis bag with a 10000 MWCO), placed in 1000 ml of dialysate at 37° C., and placed in a dissolution apparatus for dialysis at 200 rpm;
   (3) 20 μl of liposome solution in the dialysis tube was taken at 0.5 h, 2 h, 4 h, 8 h, 12 h, 24 h, 48 h, 180 μl of chromatographically pure methanol was added, and placed on the vortex for 5 min to rupture the membrane and extract all-trans retinoic acid;
   (4) The extracted methanol solution was placed in a centrifuge, centrifuged at 10,000 rpm for 30 min to precipitate the lipid material precipitated after demulsification, and 40 μl of the supernatant was taken for detection according to the HPLC conditions of the previous operation, and the cumulative release rates of the two prescriptions were compared.

Figure 3:
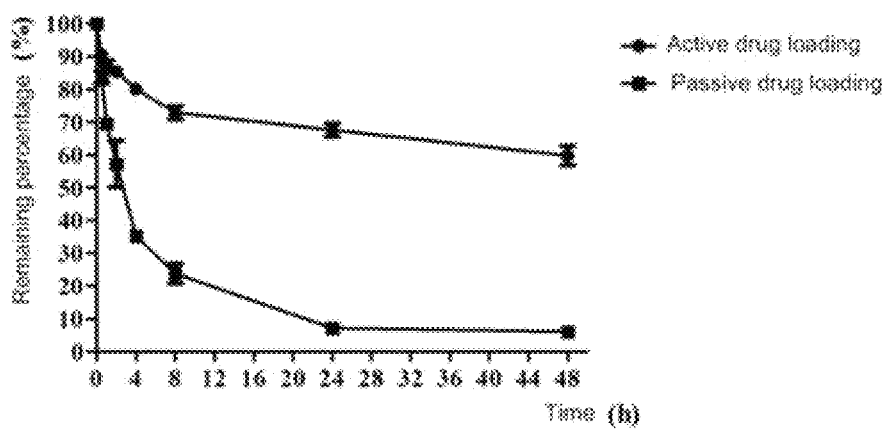
FIG. 3 shows the comparison of the cumulative release rates of two formulations.

The result was shown in FIG. 3, the all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

In addition, according to the above method, for Formula 1, all-trans retinoic acid liposomes were prepared using the corresponding passive drug loading method for comparison. The all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

In addition, according to the above method, for Formula 2, all-trans retinoic acid liposomes were prepared using the corresponding passive drug loading method for comparison. The all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

In addition, according to the above method, for Formula 3, all-trans retinoic acid liposomes were prepared using the corresponding passive drug loading method for comparison. The all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

In addition, according to the above method, for Formula 4, all-trans retinoic acid liposomes were prepared using the corresponding passive drug loading method for comparison. The all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

In addition, according to the above method, for Formula 5, all-trans retinoic acid liposomes were prepared using the corresponding passive drug loading method for comparison. The all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

In addition, according to the above method, for Formula 6, all-trans retinoic acid liposomes were prepared using the corresponding passive drug loading method for comparison. The all-trans retinoic acid liposome prepared by the active drug loading method was more advantageous in sustained release than the all-trans retinoic acid liposome prepared by the passive drug loading method. Specifically, the all-trans retinoic acid liposome in the non-calcium acetate aqueous phase was almost run out in the in vitro simulated release at 24 h, while the all-trans retinoic acid liposome in the calcium acetate aqueous phase remained 50% unreleased at 48 h.

Example 3 all-Trans Retinoic Acid (ATRA) Liposome Induces Differentiation of Myeloid-Derived Suppressor Cells (MDSC) In Vitro 1. Construction of Tumor Model in Balb/C Mice
   (1) CT-26 cells in logarithmic growth phase were digested with trypsin and collected by centrifuging at 300 g for 5 minutes. After discarding the supernatant, the cells were resuspended in sterile PBS and the concentration was adjusted to 1×107 cells/mL.
   (2) Six-week-old Balb/c mice were purchased and hairs around subcutaneous inoculation site were shaved in advanced. Mice were anesthetized by intraperitoneal injection of 200 μL of 4% chloral hydrate and the prepared 5×105 to 1×106 CT-26 cells suspension was subcutaneously injected into the right underarm region. Continue to raise after inoculation.
   (3) After 2 to 3 weeks, the long diameter (L) and short diameter (S) of the inoculated tumor were measured using a vernier caliper, and the tumor volume size (V) was calculated by the formula: V=½×L×S2. The animal experiment can be performed when the tumor volume reaches to about 100 mm3.
2. Characterization and Sorting of Tumor-associated Lymphocytes MDSCs
   (1) The mice were sacrificed by cervical dislocation, and the tumor was subcutaneously removed with forceps and scissors. The tumor tissue was cut into small pieces on a 40 μm cell strainer with gentle shearing force which can avoid from damaging the tumor cell. At the same time the tissues were continuously washed with 5% PBS during the cutting process.
   (2) All the small pieces of tissues and the PBS solution were centrifuged and the supernatant was discarded. All the mince tissues were transferred into a 15 mL centrifuge tube containing 1 mL of tissue digestion medium, and the tube was incubated on a shaker (200 rpm/minute) under 37° C. for 1 hour.
   (3) The digested cells suspension was screened again with the 40 μm cell strainer, and the cells were washed with PBS for 2 to 3 times to remove residual tissue digestion medium, cell debris and dead cells. The conditions of centrifugation were set as 1000 rpm for 5 minutes. Finally, the centrifuged cells were resuspended in PBS to obtain tumor single cell suspension.
   (4) The sorting buffer was added at a proportion of 107 cells per 90 μL volume, and CD11b microbeads were added at a proportion of 107 cells per 100 μL volume.
   (5) The microbeads and the cells were thoroughly mixed, and incubated at 4° C. for 30 minutes in the dark. After incubation, 90 μL of buffer was added per 107 cells/1 mL to wash cells by centrifugation at 1000 rpm for 5 minutes. Continue to wash for 2 times with the buffer after centrifugation.
   (6) Finally, 500 μL of buffer was added to resuspend the microbeads-binding tumor single cell suspension.
   (7) An MS column was placed in a matching magnet and fully saturated by rinsing with buffer in advance.
   (8) After rinsing, the tumor single cell suspension was applied onto the MS column, and the MS column was washed with 1 mL of buffer to remove the unlabeled cells.
   (9) After repeated washing for 3 to 5 times, the MS column was removed, placed on a 15 mL centrifuge tube and added with 1 mL of buffer. By quickly pushing a matching instrument of the MS column into the column, CD11b positive cells were collected from the MS column.
   (10) Cell counting was carried out on the CD11b positive cell suspension obtained in the previous operation and flow cytometry samples were prepared by adjusting the cell concentration to 107/mL.
   (11) Flow cytometry samples were divided into a negative sample, a Gr-1 single positive sample, a CD11b single positive sample and a test sample. In each sample group, 2 to 3 tubes were set in parallel runs. No fluorescent antibody was added to the negative sample to set a negative condition. Single fluorescent antibodies were respectively added to the Gr-1 single positive sample and the CD11b single positive sample for subsequent fluorescence compensation. A test fluorescent antibody was added to the test sample.
   (12) About 106 cells were resuspended using 100 μL of flow cytometry staining buffer in all the flow tubes. No fluorescent antibody was added in the negative sample, anti-Gr-1 antibody was added in the Gr-1 single positive sample, anti-CD11b antibody was added in the CD11b single positive sample, and anti-Gr-1 and anti-CD11b antibodies were both added in the test sample.
   (13) Flow cytometry samples were incubated at 4° C. for 30 minutes in the dark. After incubation, in order to wash away unbound antibodies, 1 mL of staining buffer was added to cells. Then the samples were centrifuged. Cells were washed twice with staining buffer before the cells were finally resuspended with 500 μL of staining buffer and proceeded to run samples on the flow cytometer.
3. All-trans Retinoic Acid Liposome Induces Differentiation of Lymphocytes in Peripheral Blood and Tumor Sites
   (1) The all-trans retinoic acid liposome was prepared according to the method of embodiment 1 (including formula 1, formula 2, formula 3, formula 4, formula 5, and formula 6).
   (2) MDSCs in the tumor tissues were sorted and the cell concentration was adjusted to 107/mL after cell counting. The collected cells after sorting were inoculated into a 24-well plate at a final concentration of 106/pore.

(3) 20 μL of PBS, 20 μL and 50 μL of ATRA-liposome were separately added in the 24-well plate containing cells, and the plate was incubated at 37° C. for 24 hours.

(4) After 1 day of incubation, the cells were incubated with Gr-1 and CD11b, CD11c, CD80, CD86 and MHC-II antibodies, and changes of MDSC and DC in the cells were observed by flow cytometry. The isotype control and fluorescence compensation were added during the flow cytometry.

Figure 4A:
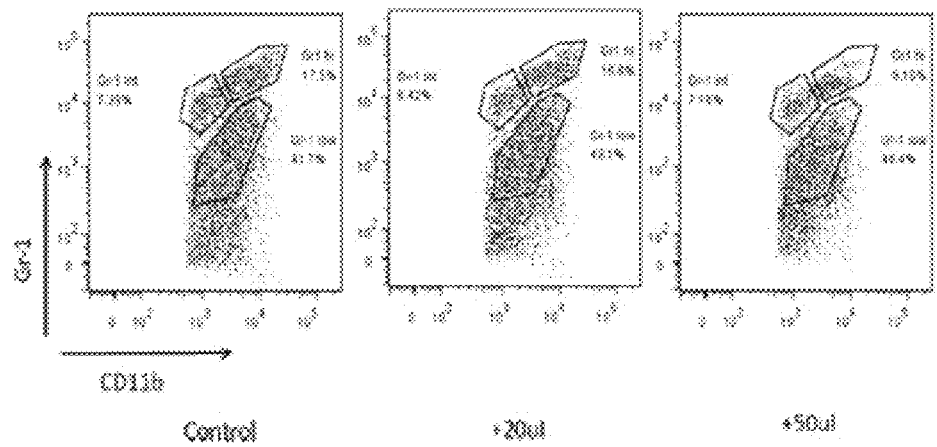
FIG. 4A shows assay for inhibition of MDSCs in mouse tumor site by Formula 1.

Formula 1: as shown in FIG. 4A, the results show that the number of Gr-1hi cells decrease significantly by administering different doses of the drug. In the high dose group (+50 μLATRA-liposome), the proportion of Gr-1hi cells decrease from 17.5% to 9.10% compared with the control group. However, the proportion of Gr-1int cells does not change much, probably because the high expression of Gr-1 was converted to medium-low expression of Gr-1 under the induction of the all-trans retinoic acid. The proportion of Gr-1low cells increases with the increasing dose of administration, which further indicates that the all-trans retinoic acid induces differentiation of MDSCs and decreases the expression of Gr-1. Since most of the infiltrating MDSCs at the tumor sites were characterized by Gr-1hi or Gr-1int, we can conclude that the all-trans retinoic acid liposome can induce differentiation of the MDSCs and decrease its numbers in the tumor sites.

Figure 4B:
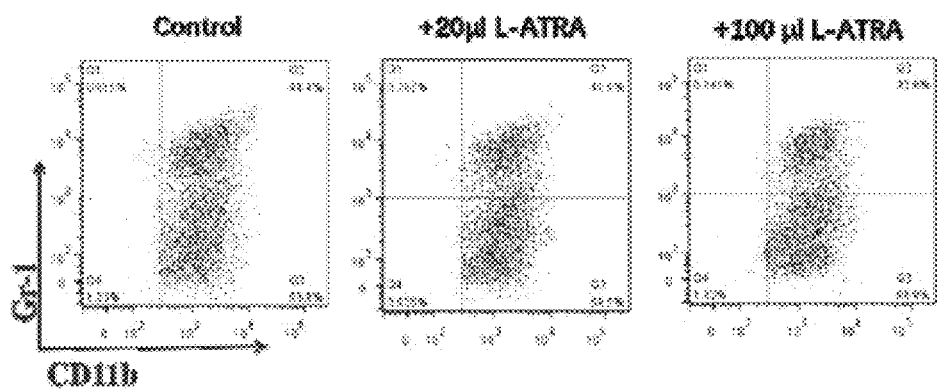
FIG. 4B shows assay for inhibition of MDSCs in mouse tumor site by Formula 6.

Formula 6: as shown in FIG. 4B, the results show that the number of CD11b+Gr-1+ cells decrease significantly by administering different doses of the drug. In the high dose group (+100 μLATRA-liposome), the proportion of CD11b+Gr-1+ cells decreases from 44.5% to 32.6% compared with the control group, which indicates that the all-trans retinoic acid induces differentiation of MDSCs and decreases the expression of Gr-1. Since most of the infiltrating MDSCs at the tumor sites were characterized by CD11b+Gr-1+, we can conclude that the all-trans retinoic acid liposome can induce differentiation of the MDSCs and decrease its numbers in the tumor sites.

Treatment with Formula 2 was consistent with the experimental result of Formula 6, the all-trans retinoic acid liposome can induce differentiation of the MDSCs and decrease its numbers in the tumor sites.

Treatment with Formula 3 was consistent with the experimental result of Formula 6, the all-trans retinoic acid liposome can induce differentiation of the MDSCs and decrease its numbers in the tumor sites.

Treatment with Formula 4 was consistent with the experimental result of Formula 6, the all-trans retinoic acid liposome can induce differentiation of the MDSCs and decrease its numbers in the tumor sites.

Treatment with Formula 5 was consistent with the experimental result of Formula 6, the all-trans retinoic acid liposome can induce differentiation of the MDSCs and decrease its numbers in the tumor sites.

Figure 5:
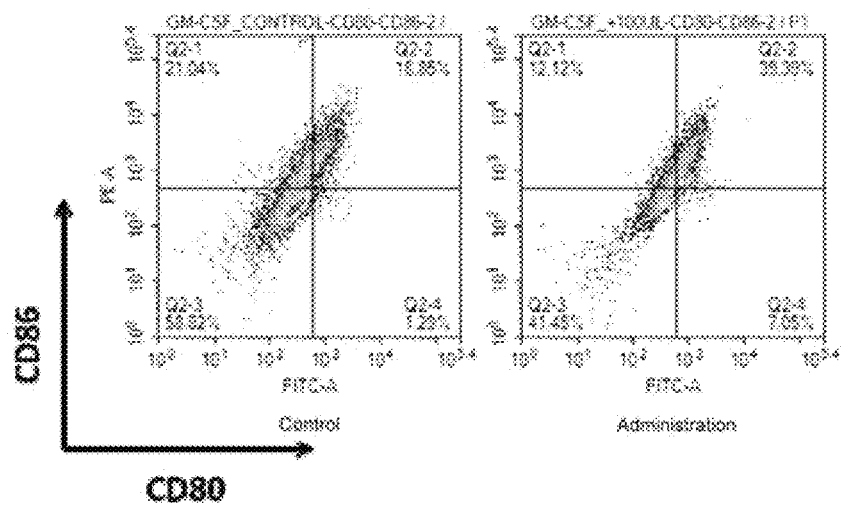
FIG. 5A shows that Formula 1 promotes differentiation of MDSCs into mature DCs in mouse tumor site.
FIG. 5B shows that Formula 1 promotes differentiation of MDSCs into mature DCs in mouse tumor site.
FIG. 5C shows that Formula 6 promotes differentiation of MDSCs into mature DCs in mouse tumor site.
FIG. 5D shows that Formula 6 promotes differentiation of MDSCs into mature DCs in mouse tumor site.
Figure 5:
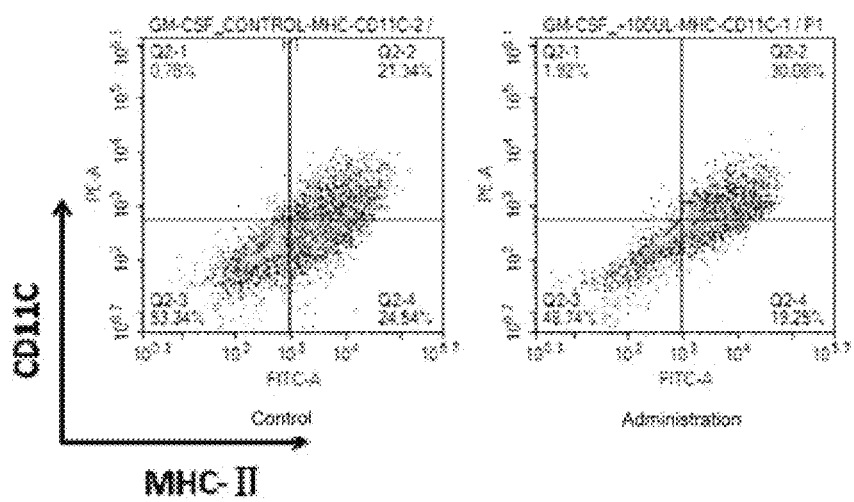

Treatment with Formula 1 was shown in FIG. 5A, the percentage of MHC-II, CD11c, CD80 and CD86 significantly increased after administration. Specially, CD80+CD86+ cells increased from 18.85% in the control group to 39.39%. As shown in FIG. 5B, MHC-II+CD11c+ cells increased from 21.34% to 30.08%.

Figure 5C:
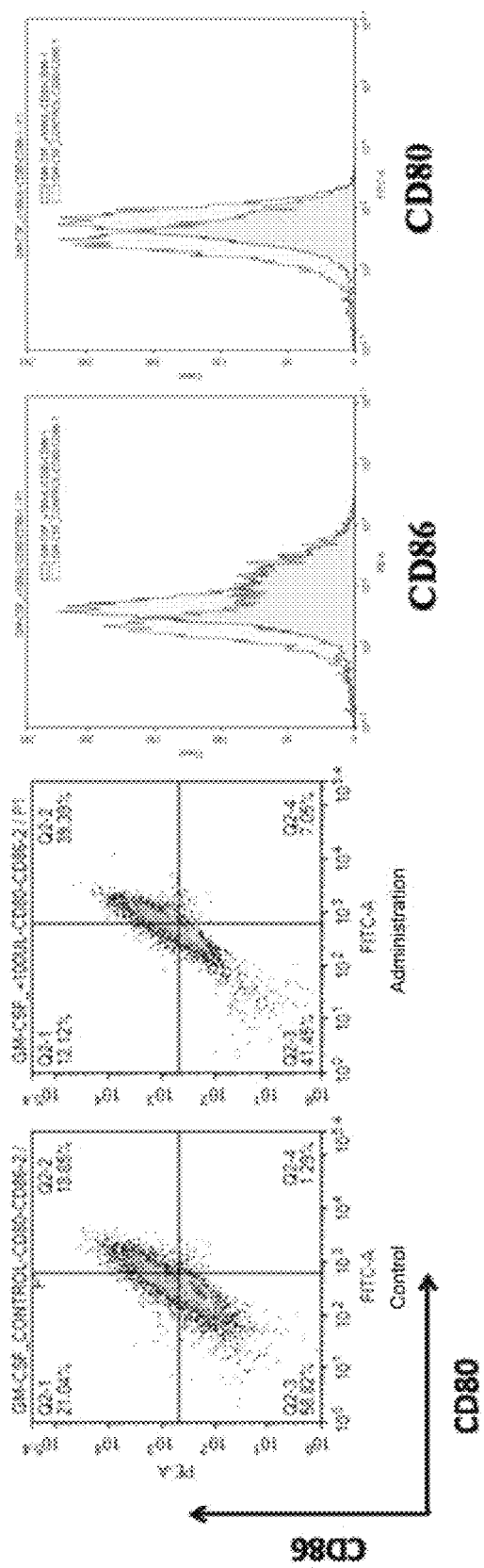
Figure 5D:
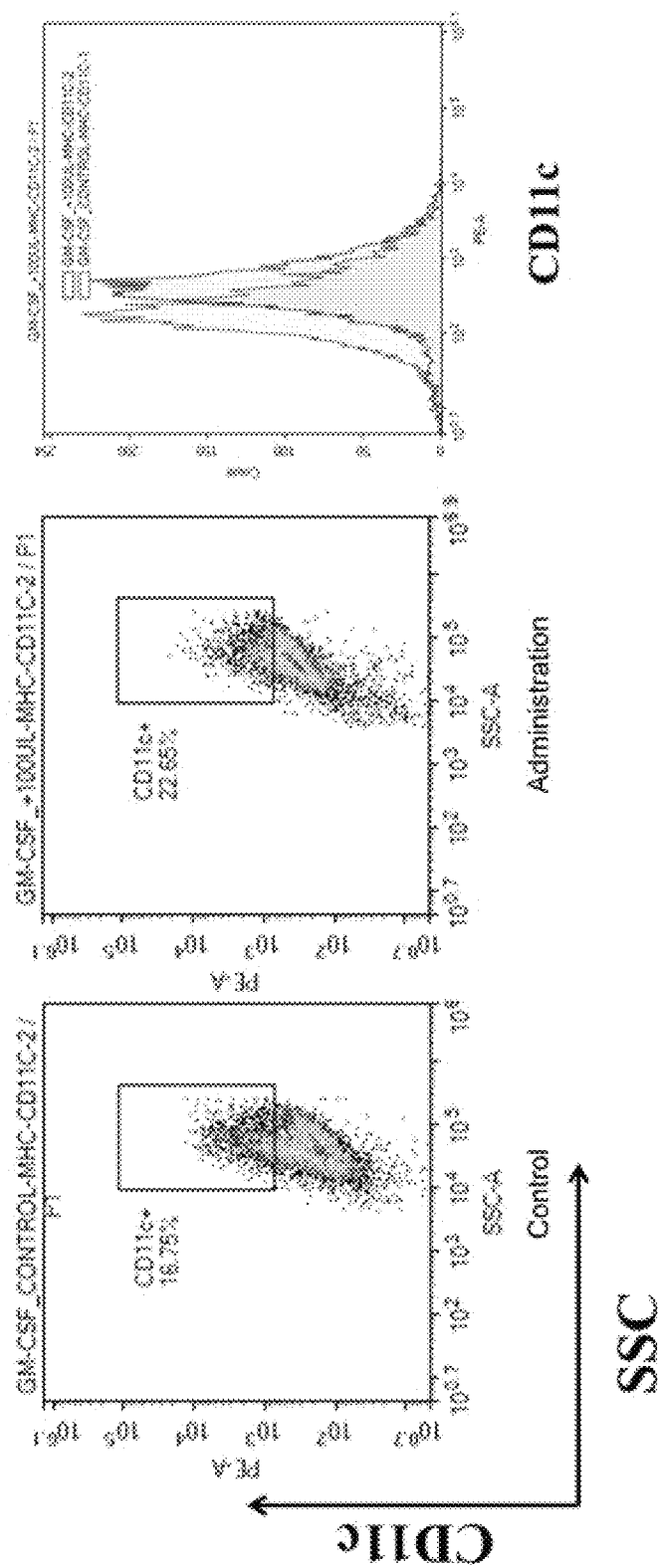

Treatment with Formula 6 was shown in FIG. 5C, the percentage of MHC-II, CD11c, CD80 and CD86 significantly increased after administration. Specially, CD80+CD86+ cells increased from 18.85% to 39.39%. As shown in FIG. 5D, MHC-II+ cells increased from 16.75% to 22.65%, and CD11c+ cells increased from 45.83% to 49.27%.

Treatment with Formula 2 was consistent with the experimental result of Formula 6.

Treatment with Formula 3 was consistent with the experimental result of Formula 6.

Treatment with Formula 4 was consistent with the experimental result of Formula 6.

Treatment with Formula 5 was consistent with the experimental result of Formula 6.

Example 4 all-Trans Retinoic Acid Liposome Promotes Proliferation of T Cells in PBMC from Patients with Head and Neck Mucosal Squamous Cell Carcinoma (HNSCC 2 mL of anticoagulation was taken and diluted twice with 2 mL of PBS. The diluted blood was carefully layered on 3 mL of a human lymphocyte separation solution along the inner wall of the test tube. The sample was centrifuged at 300 g for 30 minutes at room temperature (acceleration 2, deceleration 1). The mononuclear cell layer was carefully transferred to a tube and washed twice with 10 mL PBS buffer at 300 g. After the supernatant was discarded, a small amount of PBS was added to obtain a big amount of PBMC, which was maintained at 4° C. for further application. According to the microbeads separation equipment operating manual, myeloid-derived cells in the PBMC are separated by CD33+ microbeads. Cells are cultured in 12-well plate at 5×105 cells/well with RPM11640 complete medium (10% FBS added). The all-trans retinoic acid injectable formulation prepared as described in embodiment 1 was added and the cell plate was cultured for 24 hours. Then the percentage of HLA-DR+CD11c+ phenotypic DC cells population in myeloid-derived cells was detected by flow cytometry.

Figure 6A:
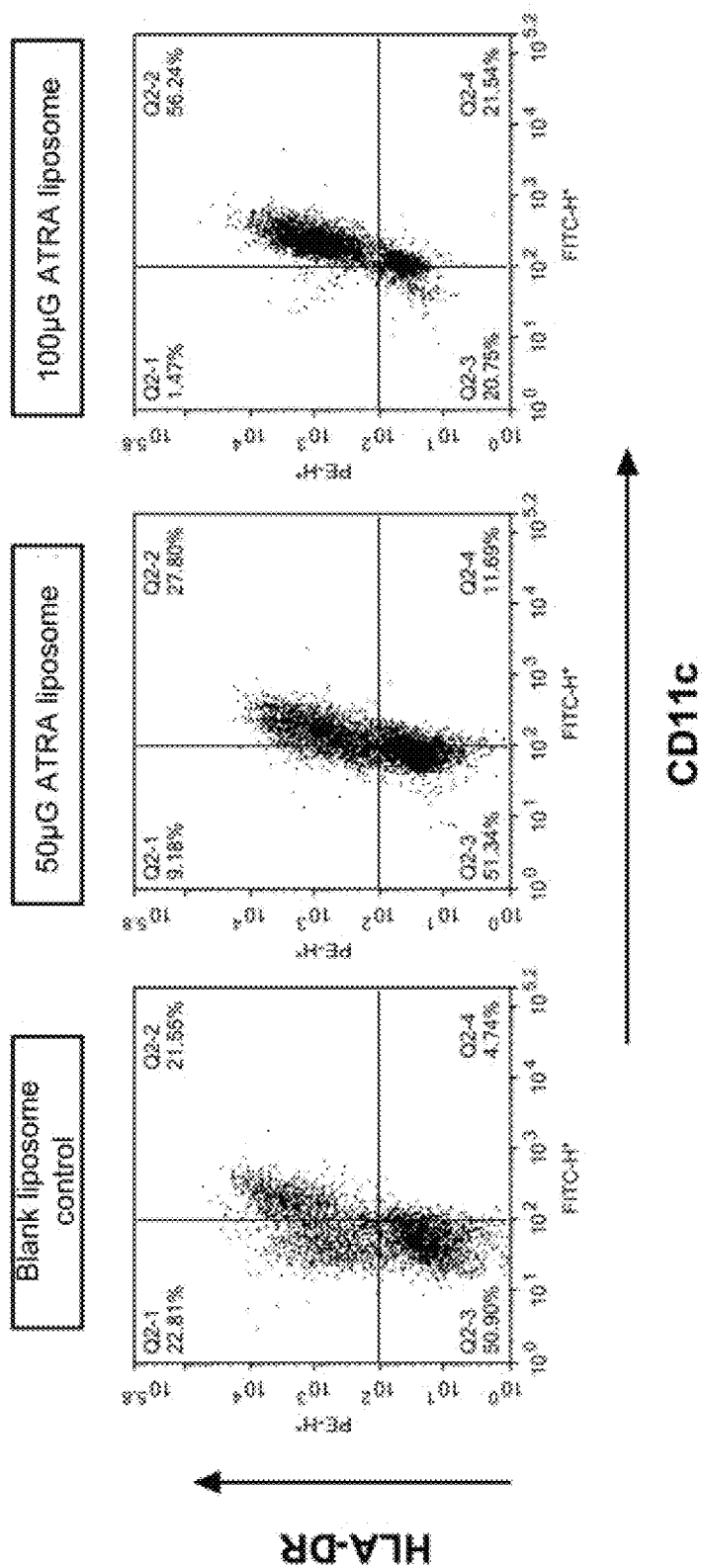
FIG. 6A shows that Formula 1 of the present disclosure promotes differentiation of MDSCs into DC-like cells in the blood of patients with head and neck mucosal squamous cell carcinoma.

Treatment with Formula 1 was shown in FIG. 6A, it acts with PBMC in the blood of a patient with head and neck mucosal squamous cell carcinoma, the all-trans retinoic acid liposome of the present disclosure promotes differentiation of MDSCs into DC-type cells.

Figure 6B:
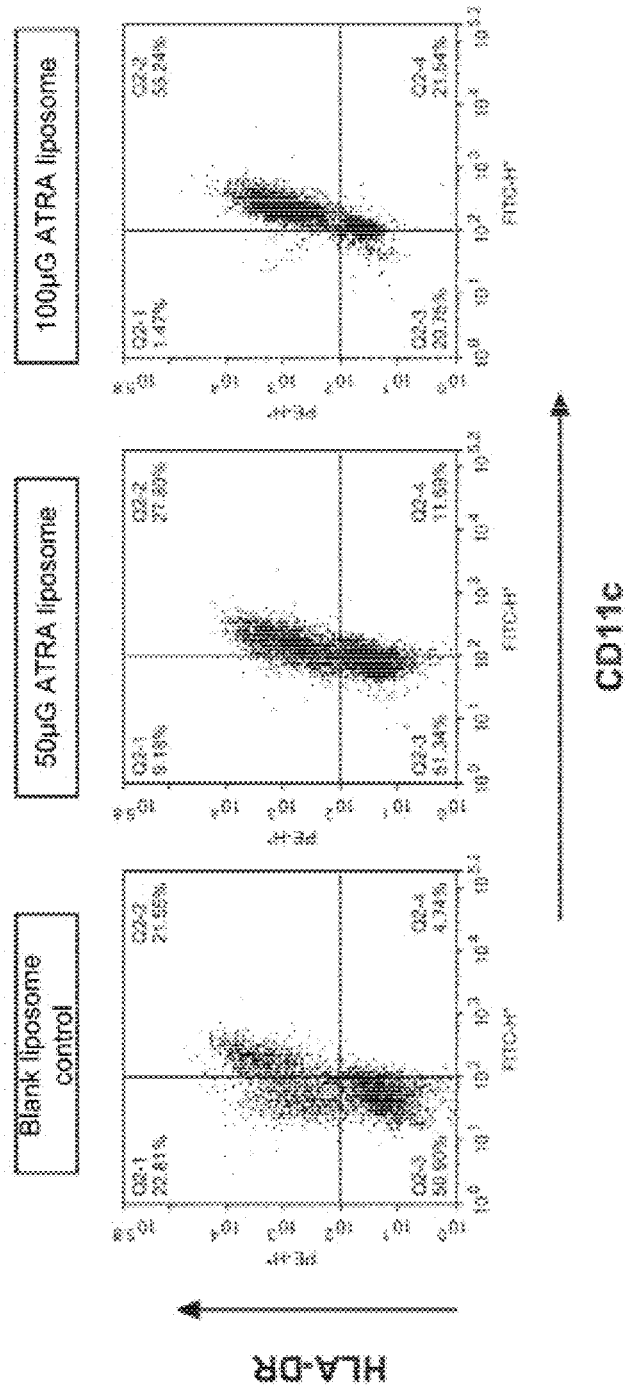
FIG. 6B shows that Formula 6 of the present disclosure promotes differentiation of MDSCs into DC-like cells in the blood of patients with head and neck mucosal squamous cell carcinoma.

Treatment with Formula 6 was shown in FIG. 6B, it acts with PBMC in the blood of a patient with head and neck mucosal squamous cell carcinoma, the all-trans retinoic acid liposome of the present disclosure promotes differentiation of MDSCs into DC-type cells.

Treatment with Formula 2 was consistent with the experimental result of Formula 6, it acts with PBMC in the blood of a patient with head and neck mucosal squamous cell carcinoma, the all-trans retinoic acid liposome of the present disclosure promotes differentiation of MDSCs into DC-type cells.

Treatment with Formula 3 was consistent with the experimental result of Formula 6, it acts with PBMC in the blood of a patient with head and neck mucosal squamous cell carcinoma, the all-trans retinoic acid liposome of the present disclosure promotes differentiation of MDSCs into DC-type cells.

Treatment with Formula 4 was consistent with the experimental result of Formula 6, it acts with PBMC in the blood of a patient with head and neck mucosal squamous cell carcinoma, the all-trans retinoic acid liposome of the present disclosure promotes differentiation of MDSCs into DC-type cells.

Treatment with Formula 5 was consistent with the experimental result of Formula 6, it acts with PBMC in the blood of a patient with head and neck mucosal squamous cell carcinoma, the all-trans retinoic acid liposome of the present disclosure promotes differentiation of MDSCs into DC-type cells.

Example 5 all-Trans Retinoic Acid Liposome Significantly Reduces the Number of CD33+HLA-DR-MDSCs in Tumor-Infiltrating Myeloid-Derived Cells from Bladder Cancer Patients Surrounding necrotic tissue was eliminated to reduce the impact to the experiment, the clinic tumor sample was rinsed with sterile saline and placed in a RPMI 1640 medium containing penicillin 100 μg/mL, streptomycin 100 μg/mL and 10% fetal bovine serum at 4° C. before laboratory treatment. The tumor tissue was cut into small pieces in medium on ice, then transferred to a 15 mL centrifuge tube containing 2 mL of enzyme digestive fluid (0.6 to 1 mg/mL collagenase I and IV digestive fluid) and gently swirled. The mince tissues mixture was incubated on a shaker (200 rpm/minutes) under 37° C. for 2 hours. The suspension was then slowly washed with sterile PBS, screened with the 40 μm membrane, and transferred to a 50 ml centrifuge tube. The conditions of centrifugation were set as 300 g for 10 minutes. Finally, the centrifuged cells were resuspended in PBS and counted. According to the microbeads separation equipment operating manual, myeloid-derived cells in the tumor tissue infiltrating cells were separated by CD33+ microbeads. Collected myeloid-derived cells were cultured in 12-well plate at 5×105 cells/well with RPM11640 complete medium (10% FBS added). The all-trans retinoic acid injectable formulation prepared as described in embodiment 1 was added and the cell plate was cultured for 24 hours. Then the percentage of CD33+HLA-DR-MDSCs population in myeloid-derived cells was detected by flow cytometry.

Figure 7A:
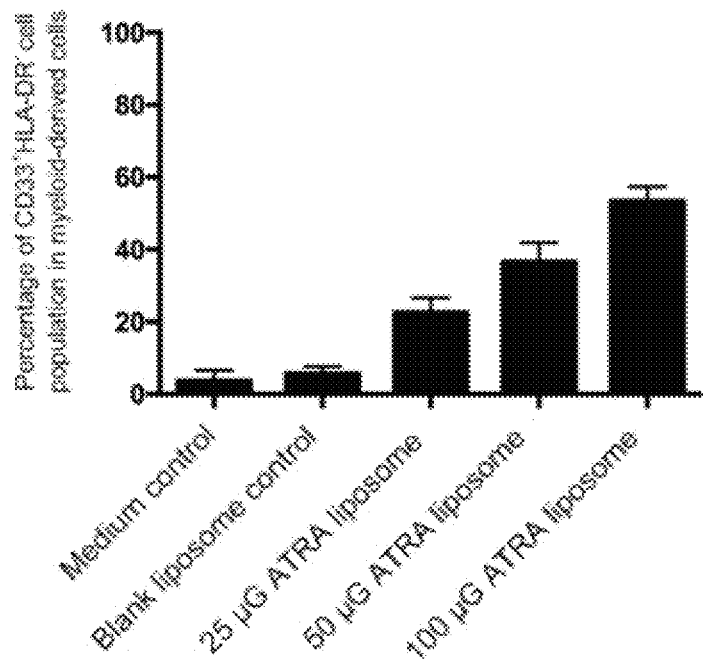
FIG. 7A shows that Formula 1 of the present disclosure acts on tumor tissues in tumor patients, and can significantly reduce the number of CD33+HLA-DR-MDSC in the tumor infiltrating myeloid-derived cells of bladder cancer.
Figure 8A:
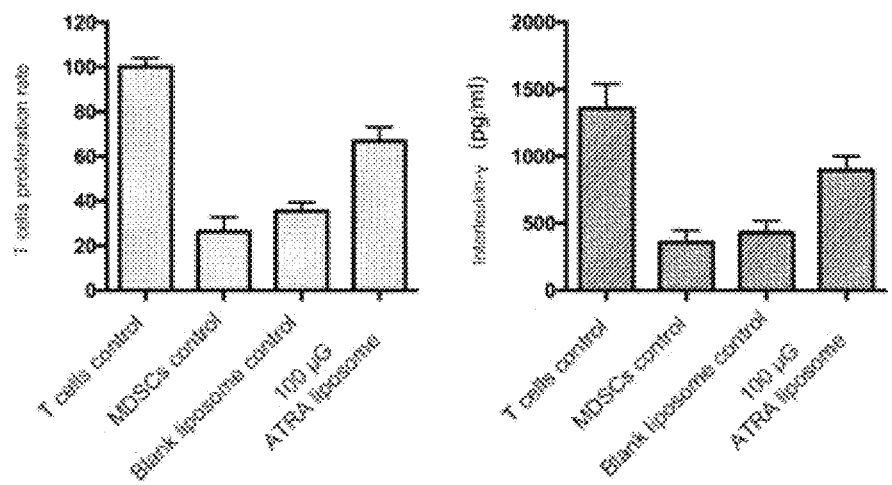
FIG. 8A shows that Formula 1 of the present disclosure acts on tumor tissues in tumor patients and promotes T cells proliferation in head and neck mucosal squamous cell carcinoma PBMC.

For formula 1, the result was shown in FIG. 7A, the all-trans retinoic acid liposome prepared in the present disclosure can significantly reduce the number of CD33+ HLA-DR-MDSCs in tumor infiltrating myeloid-derived cells derived from bladder cancer patient. As shown in FIG. 8A, the all-trans retinoic acid liposome prepared in the present disclosure can promote the proliferation of T cells in head and neck mucosal squamous cell carcinoma PBMC.

Figure 7B:
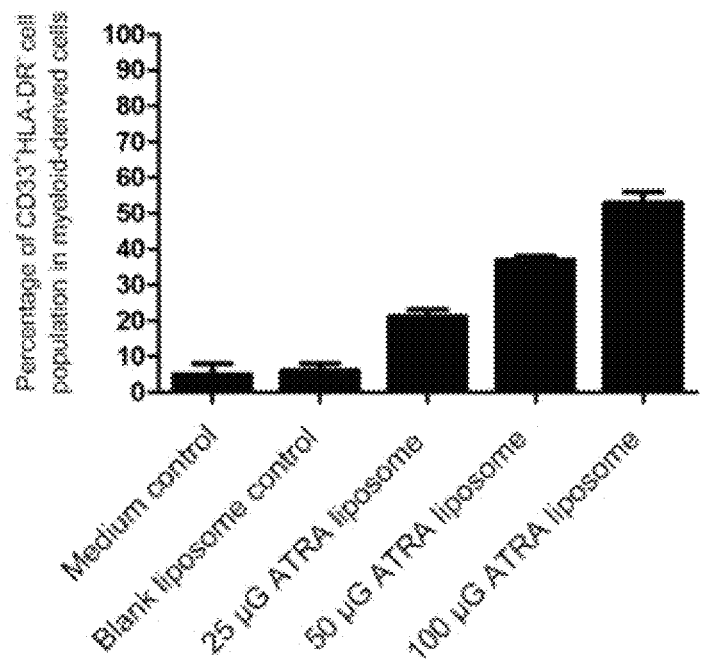
FIG. 7B shows that Formula 6 of the present disclosure acts on tumor tissues in tumor patients, and can significantly reduce the number of CD33+HLA-DR-MDSC in the tumor infiltrating myeloid-derived cells of bladder cancer.
Figure 8B:
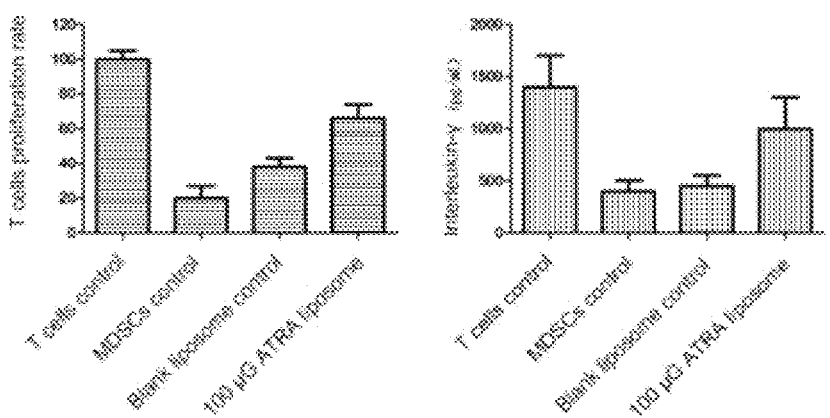
FIG. 8B shows that Formula 6 of the present disclosure acts on tumor tissues in tumor patients and promotes T cells proliferation in head and neck mucosal squamous cell carcinoma PBMC.

For formula 6, the result was shown in FIG. 7B, the all-trans retinoic acid liposome prepared in the present disclosure can significantly reduce the number of CD33+ HLA-DR-MDSCs in tumor infiltrating myeloid-derived cells derived from bladder cancer patient. As shown in FIG. 8B, the all-trans retinoic acid liposome prepared in the present disclosure can promote the proliferation of T cells in head and neck mucosal squamous cell carcinoma PBMC.

For formula 2, the result was consistent with that of Formula 6, the all-trans retinoic acid liposome prepared in the present disclosure can significantly reduce the number of CD33+HLA-DR-MDSCs in tumor infiltrating myeloid-derived cells derived from bladder cancer patient. The all-trans retinoic acid liposome prepared in the present disclosure can promote the proliferation of T cells in head and neck mucosal squamous cell carcinoma PBMC.

For formula 3, the result was consistent with that of Formula 6, the all-trans retinoic acid liposome prepared in the present disclosure can significantly reduce the number of CD33+HLA-DR-MDSCs in tumor infiltrating myeloid-derived cells derived from bladder cancer patient. The all-trans retinoic acid liposome prepared in the present disclosure can promote the proliferation of T cells in head and neck mucosal squamous cell carcinoma PBMC.

For formula 4, the result was consistent with that of Formula 6, the all-trans retinoic acid liposome prepared in the present disclosure can significantly reduce the number of CD33+HLA-DR-MDSCs in tumor infiltrating myeloid-derived cells derived from bladder cancer patient. The all-trans retinoic acid liposome prepared in the present disclosure can promote the proliferation of T cells in head and neck mucosal squamous cell carcinoma PBMC.

For formula 5, the result was consistent with that of Formula 6, the all-trans retinoic acid liposome prepared in the present disclosure can significantly reduce the number of CD33+HLA-DR-MDSCs in tumor infiltrating myeloid-derived cells derived from bladder cancer patient. The all-trans retinoic acid liposome prepared in the present disclosure can promote the proliferation of T cells in head and neck mucosal squamous cell carcinoma PBMC.

Example 6 Pharmacokinetic Data with Intravenous Injection with all-Trans Retinoic Acid Liposome with Metabolic Half Life Reached 8~12 h (1) Preparing the ATRA Liposome described in Example 1. Formula 1 was taken and measured of the drug concentration.

(2) A total of three SD rats were purchased from Beijing Vital River Laboratory Animal Technology Co., Ltd., numbered IV-1, IV-2, IV-3. Before the experiment, the SD rats were kept fasted overnight. On the day of the experiment, group A SD rats were injected with 10 mg×kg-1 of all-trans retinoic acid liposome in the tail vein. 0.2 mL of blood was collected from jugular vein at the time point of 5 min, 15 min, 30 min, 1 h, 2 h, 4 h, 8 h, 24 h and 48 h respectively.

The blood samples were transferred to clean heparin sodium precoating eppendorf tubes and centrifuged for 5500 rpm for 10 min, after which upper layer (plasma) was collected and stored in a refrigerator below −20° C. SD Rats resumed feeding 4 hours after administration while water drinking freely during the experiment.

(3) Drug concentration in the plasma were detected by LC/MS. Biological analysis according to SOP-RS-04-001/01(Bioanalytical Method Validation for Quantification of Early Drug Discovery Compounds Using LC-MS/MS Methods, 3D BioOptima Co., Ltd), LC-MS/MS method used for determination was established by 3D BioOptima Co., Ltd. Pharmacokinetic parameters were calculated using the non-atrioventricular model in Pharsight Phoenix 6.3. Table 1-1 shows the Pharmacokinetic Parameters with i.v. of Formula 1.

TABLE 1-1

PK data of rats administered by tail vein injection of Formula 1

| PK Parameters | Unit | IV-1 | IV-2 | IV-3 | Mean | SD | CV (%) |
|---|---|---|---|---|---|---|---|
| $K_{el}$ | $h^{-1}$ | 0.0847 | 0.0924 | 0.0797 | 0.0856 | 0.0064 | 7.5 |
| T1/2 | h | 8.2 | 7.5 | 8.7 | 8.1 | 0.6 | 7.4 |
| $AUC_{0-t}$ | $ng \cdot h \cdot mL^{-1}$ | 20139 | 21549 | 18420 | 20036 | 1567 | 7.8 |
| $AUC_{0-inf}$ | $ng \cdot h \cdot mL^{-1}$ | 20224 | 21633 | 18533 | 20130 | 1552 | 7.7 |
| $AUMC_{0-t}$ | $ng \cdot h^2 \cdot mL^{-1}$ | 29314 | 30993 | 27470 | 29259 | 1762 | 6.0 |
| $AUMC_{0-inf}$ | $ng \cdot h^2 \cdot mL^{-1}$ | 32391 | 33942 | 31589 | 32641 | 1196 | 3.7 |
| $MRT_{IV}$ | h | 1.6 | 1.6 | 1.7 | 1.6 | 0.1 | 4.4 |
| CL | $mL \cdot kg^{-1} \cdot min^{-1}$ | 8.24 | 7.70 | 8.99 | 8.31 | 0.65 | 7.8 |
| $Vd_{ss}$ | $L \cdot kg^{-1}$ | 0.792 | 0.725 | 0.920 | 0.812 | 0.099 | 12 |

Figure 9:
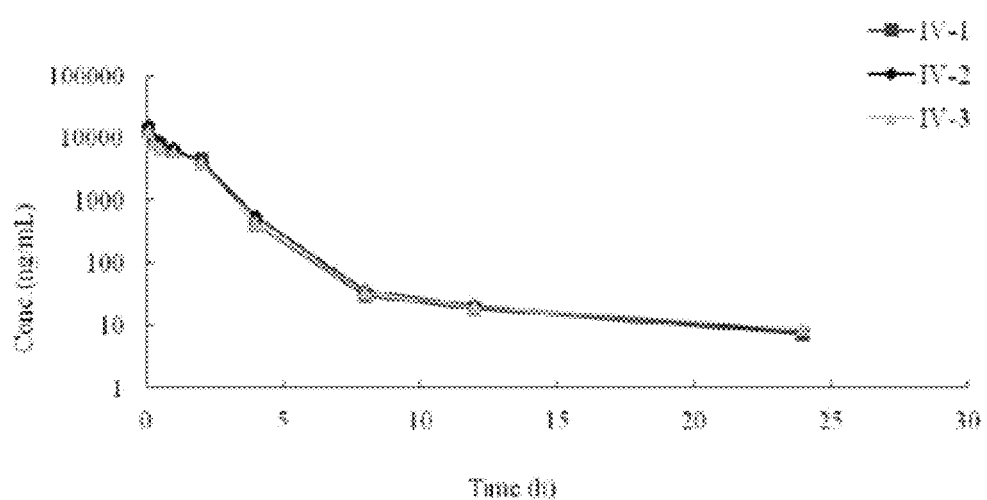
FIG. 9 shows the PK curve graph of rats in Example 6 administered by tail vein injection.

As shown in Table 1-1 and FIG. 9, the plasma metabolic half life of Formula 1 can reach 8~12 hours.

Formula 2-Formula 6 were followed the same protocol above and pharmacokinetic parameters were shown in table 1-2.

TABLE 1-2

Pharmacokinetic Parameters

| PK Parameters | Unit | Formula 2 | Formula 3 | Formula 4 | Formula 5 | Formula 6 |
|---|---|---|---|---|---|---|
| $K_{el}$ | $h^{-1}$ | 0.0797 | 0.0847 | 0.0909 | 0.100 | 0.0810 |
| T1/2 | h | 8.7 | 8.2 | 7.7 | 6.9 | 9.0 |
| $AUC_{0-t}$ | $ng \cdot h \cdot mL^{-1}$ | 18420 | 20139 | 35216 | 32178 | 18550 |
| $AUC_{0-inf}$ | $ng \cdot h \cdot mL^{-1}$ | 18533 | 20224 | 35256 | 32201 | 18600 |
| $AUMC_{0-t}$ | $ng \cdot h^2 \cdot mL^{-1}$ | 27470 | 29314 | 54796 | 46131 | 27600 |
| $AUMC_{0-inf}$ | $ng \cdot h^2 \cdot mL^{-1}$ | 31589 | 32391 | 56191 | 46927 | 31570 |
| $MRT_{IV}$ | h | 1.7 | 1.6 | 1.6 | 1.5 | 1.8 |
| CL | $mL \cdot kg^{-1} \cdot min^{-1}$ | 8.99 | 8.24 | 3.53 | 3.81 | 8.99 |
| $Vd_{ss}$ | $L \cdot kg^{-1}$ | 0.920 | 0.792 | 0.334 | 0.333 | 0.925 |

As shown in Table 1-2, it can be concluded that the plasma metabolic half life of Formula 2-Formula 6 could reach 8~12 h.

Example 7 all-Trans Retinoic Acid Formulation Containing Different Solubilizers

1. All-trans Retinoic Acid Liposome Containing Hydroxypropyl-β-Cyclodextrin in Aqueous Phase (1) 121.742 mg of HSPC (molecular weight: 783.8), 38.22 mg of DSPE-PEG2000, and 40.04 mg of cholesterol were weighed and dissolved in 1.6 mL of ethanol, and water bathed to be dissolved and mixed at 70° C. in a water bath to obtain an ethanol mixture.

(2) The obtained ethanol mixture from operation (1) was then added with 6.4 mL calcium acetate buffer (PH 9.0, which consisted of 200 mM calcium acetate, hydroxypropyl-β-cyclodextrin, and water) containing hydroxypropyl-β-cyclodextrin (12%, w/v), and water bathed at 70° C. for 30 minutes to obtain liposome vesicles.

(3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 90 nm and an aqueous phase of calcium acetate.

(4) The liposome prepared in operation (3) was dialyzed through a dialysis membrane with a 10000 MWCO (Molecular Weight Cut off) in a 10% sucrose aqueous solution (pH 6~7), and the outer aqueous phase of the liposome was replaced with a 10% sucrose aqueous solution (pH 6~7) to obtain a calcium acetate liposome having a phospholipid bilayer membrane, and the inner aqueous phase and outer aqueous phase of the bilayer membrane have a certain pH gradient and an ion gradient. Specifically, the inner aqueous phase of the bilayer membrane was an aqueous solution of calcium acetate (pH 9.0, concentration: 200 mM), and the outer aqueous phase of the bilayer membrane was a sucrose aqueous solution (pH 6~7, mass fraction of 10%).

(5) 5 mg/mL suspension of all-trans retinoic acid was added to the calcium acetate liposome obtained from operation (4), the volume ratio of the added suspension of all-trans retinoic acid to the calcium acetate liposome was 1:1, and the mixture was incubated for 45 minutes at 60° C. After incubation, the free all-trans retinoic acid not loading into the liposome was removed by the dialysis membrane with a 10000 MWCO, and the final all-trans retinoic acid liposome was obtained.

(6) The concentration of all-trans retinoic acid was determined by high performance liquid chromatography with a UV detector.

When the molar ratio of hydroxypropyl-β-cyclodextrin to all-trans retinoic acid was 2:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-β-cyclodextrin, and water) containing hydroxypropyl-β-cyclodextrin (4%, w/v), and water bathed at 70° C. for 30 minutes to obtain liposome vesicles.

When the molar ratio of hydroxypropyl-β-cyclodextrin to all-trans retinoic acid was 20:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-β-cyclodextrin, and water) containing hydroxypropyl-β-cyclodextrin (40%, w/v), and water bathed at 70° C. for 30 minutes to obtain liposome vesicles.

In addition, all-trans retinoic acid liposomes could be prepared by the above method when one or more of the other different trapping solubilizers were contained inside the aqueous phase of the liposome.

2. When the inner aqueous phase of the liposome containing hydroxypropyl methylcellulose (HPMC), all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, HPMC, and water) containing HPMC (1%, w/v), and water bathed at 70° C. for 30 minutes to obtain liposome vesicles.

3. When the inner aqueous phase of the liposome containing polyvinyl pyrrolidone (PVP), all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, PVP, and water) containing PVP (2%, w/v), and water bathed at 70° C. for 30 minutes to obtain liposome vesicles.

When the molar ratio of PVP to all-trans retinoic acid was 0.075:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, PVP, and water) containing PVP (1%, w/v), and water bathed at 70° C. for 30 minutes to obtain liposome vesicles.

When the molar ratio of PVP to all-trans retinoic acid was 1.5:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, PVP, and water) containing PVP (20%, w/v), and water bathed at 70° C. for 30 minutes to obtain liposome vesicles.

4. When the inner aqueous phase of the liposome containing polyethylene glycol 400 (PEG-400), all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, PEG-400, and water) containing PEG-400(17%, w/v), and water bathed at 70° C. for 30 minutes to obtain liposome vesicles.

When the molar ratio of PEG-400 to all-trans retinoic acid was 9.5:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, PEG-400, and water) containing PEG-400(5%, w/v), and water bathed at 70° C. for 30 minutes to obtain liposome vesicles.

When the molar ratio of PEG-400 to all-trans retinoic acid was 37.5:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, PEG-400, and water) containing PEG-400(20%, w/v), and water bathed at 70° C. for 30 minutes to obtain liposome vesicles.

5. When the inner aqueous phase of the liposome containing polyethylene glycol 400 (PEG-400) and hydroxypropyl-β-cyclodextrin, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-β-cyclodextrin, PEG-400, and water) containing hydroxypropyl-β-cyclodextrin (12%, w/v)+PEG-400(5%, w/v), and water bathed at 70° C. for 30 minutes to obtain liposome vesicles.

6. When the inner aqueous phase of the liposome containing hydroxypropyl methylcellulose (HPMC) and hydroxypropyl-β-cyclodextrin, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-β-cyclodextrin, HPMC, and water) containing hydroxypropyl-β-cyclodextrin (12%, w/v)+HPMC (0.5%, w/v), and water bathed at 70° C. for 30 minutes to obtain liposome vesicles.

7. When the inner aqueous phase of the liposome containing polyvinyl pyrrolidone (PVP) and hydroxypropyl-β-cyclodextrin, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-β-cyclodextrin, PVP, and water) containing hydroxypropyl-β-cyclodextrin (12%, w/v)+PVP (0.5%, w/v), and water bathed at 70° C. for 30 minutes to obtain liposome vesicles.

8. When the inner aqueous phase of the liposome containing sulfobutyl ether-β-cyclodextrin, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, sulfobutyl ether-β-cyclodextrin, and water) containing sulfobutyl ether-β-cyclodextrin (10%, w/v), and water bathed at 70° C. for 30 minutes to obtain liposome vesicles.

When the molar ratio of sulfobutyl ether-β-cyclodextrin to all-trans retinoic acid was 2:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, sulfobutyl ether-β-cyclodextrin, and water) containing sulfobutyl ether-β-cyclodextrin (4%, w/v), and water bathed at 70° C. for 30 minutes to obtain liposome vesicles.

When the molar ratio of sulfobutyl ether-β-cyclodextrin to all-trans retinoic acid was 20:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, sulfobutyl ether-β-cyclodextrin, and water) containing sulfobutyl ether-β-cyclodextrin (40%, w/v), and water bathed at 70° C. for 30 minutes to obtain liposome vesicles.

9. When the inner aqueous phase of the liposome containing methyl-β-cyclodextrin, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, methyl-β-cyclodextrin, and water) containing methyl-β-cyclodextrin (20%, w/v), and water bathed at 70° C. for 30 minutes to obtain liposome vesicles.

When the molar ratio of methyl-β-cyclodextrin to all-trans retinoic acid was 2:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, methyl-β-cyclodextrin, and water) containing methyl-β-cyclodextrin (4%, w/v), and water bathed at 70° C. for 30 minutes to obtain liposome vesicles.

When the molar ratio of methyl-β-cyclodextrin to all-trans retinoic acid was 20:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, methyl-β-cyclodextrin, and water) containing methyl-β-cyclodextrin (40%, w/v), and water bathed at 70° C. for 30 minutes to obtain liposome vesicles.

10. When the inner aqueous phase of the liposome containing hydroxypropyl-γ-cyclodextrin, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-γ-cyclodextrin, and water) containing hydroxypropyl-γ-cyclodextrin (12%, w/v), and water bathed at 70° C. for 30 minutes to obtain liposome vesicles.

When the molar ratio of hydroxypropyl-γ-cyclodextrin to all-trans retinoic acid was 2:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-γ-cyclodextrin, and water) containing hydroxypropyl-γ-cyclodextrin (4%, w/v), and water bathed at 70° C. for 30 minutes to obtain liposome vesicles.

When the molar ratio of hydroxypropyl-γ-cyclodextrin to all-trans retinoic acid was 20:1, all-trans retinoic acid liposomes were prepared as described above with operation (2) modified as follows: the obtained ethanol mixture from operation (1) was added with 6.4 mL calcium acetate buffer (PH 9.0, which consisted of 200 mM calcium acetate, hydroxypropyl-γ-cyclodextrin, and water) containing hydroxypropyl-γ-cyclodextrin (40%, w/v), and water bathed at 70° C. for 30 minutes to obtain liposome vesicles.

TABLE 2

| Trapping Solubilizers Contained in Inner Aqueous Phase of Liposome | Concentration(ATRA) |
|---|---|
| HPMC (1%, w/v) | 0.7 mg/ml |
| Hydroxypropyl-β-cyclodextrin (12%, w/v) + HPMC (0.5%, w/v) | 1.4 mg/ml |
| PEG-400 (17%, w/v) | 0.3 mg/ml |
| PEG-400 (5%, w/v) | 0.18 mg/ml |
| PEG-400 (20%, w/v) | 0.35 mg/ml |
| Hydroxypropyl-β-cyclodextrin (12%, w/v) + PEG-400 (5%, w/v) | 1.2 mg/ml |
| Hydroxypropyl-β-cyclodextrin (12%, w/v) | 1.6 mg/ml |
| Hydroxypropyl-β-cyclodextrin (4%, w/v) | 1.6 mg/ml |
| Hydroxypropyl-β-cyclodextrin (40%, w/v) | 1.55 mg/ml |
| PVP (1%, w/v) | 0.5 mg/ml |
| PVP (2%, w/v) | 0.52 mg/ml |
| PVP (20%, w/v) | 0.49 mg/ml |
| Hydroxypropyl-β-cyclodextrin (12%, w/v) + PVP (0.5%, w/v) | 1.1 mg/ml |
| Sulfobutyl ether-β-cyclodextrin (10%, w/v) | 1.4 mg/ml |
| Sulfobutyl ether-β-cyclodextrin (4%, w/v) | 1.35 mg/ml |
| Sulfobutyl ether-β-cyclodextrin (40%, w/v) | 1.28 mg/ml |
| Methyl-β-cyclodextrin (20%, w/v) | 1.37 mg/ml |
| Methyl-β-cyclodextrin (4%, w/v) | 1.35 mg/ml |
| Methyl-β-cyclodextrin (40%, w/v) | 1.15 mg/ml |
| Hydroxypropyl-γ-cyclodextrin (12%, w/v) | 1.65 mg/ml |
| Hydroxypropyl-γ-cyclodextrin (4%, w/v) | 1.55 mg/ml |
| Hydroxypropyl-γ-cyclodextrin (40%, w/v) | 1.40 mg/ml |

Example 8 Preparation of all-Trans Retinoic Acid Liposome with Internal Aqueous Phase Containing Sodium Acetate 1. Preparation
   (1) 0.097 g of HSPC (molecular weight: 783.8), 0.031 g of DSPE-PEG2000, and 0.031 g of cholesterol were weighed and dissolved in 1.6 mL of ethanol, and water bathed to be dissolved and mixed at 70° C. in a water bath to obtain an ethanol mixture.
   (2) The obtained ethanol mixture from operation (1) was then added with 6.4 mL of 200 mM sodium acetate buffer (PH 9.0) containing 20% cyclodextrin molecules, and water bathed at 70° C. for 30 minutes to obtain liposome vesicles.
   (3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 90 nm and an aqueous phase of sodium acetate.
   (4) The liposome prepared in operation (3) was dialyzed through a dialysis membrane with a 10000 MWCO in a 10% sucrose aqueous solution (pH 6~7), and the outer aqueous phase of the liposome was replaced with a 10% sucrose aqueous solution (pH 6~7), to obtain a liposome having a phospholipid bilayer membrane, and the inner aqueous phase and outer aqueous phase of the bilayer membrane have a certain concentration gradient of sodium acetate and cyclodextrin.

(5) 10 mg/mL suspension of all-trans retinoic acid was added to the sodium acetate liposome obtained from operation (4), the mixture was incubated for 45 minutes at 60° C. After incubation, the free all-trans retinoic acid not loading into the liposome was removed by the dialysis membrane with a 10000 MWCO, and the final all-trans retinoic acid liposome was obtained, which was labeled as Formula 7.

2. Identification of Encapsulation Efficiency of the All-trans Retinoic Acid Liposome The purified all-trans retinoic liposome formulation was destroyed with 9 volumes of methanol, and the encapsulation efficiency was determined by high performance liquid chromatography of a UV detector. Measurement conditions: ODS column (Diamonsil, 5 μm, 250×4.6 mm); detection temperature was 25° C.; detection wavelength was 340 nm; flow rate was 1.0 ml/min; mobile phase of acetonitrile/methanol (volume ratio was 95:5). The encapsulation efficiency (EE) of all-trans retinoic acid was calculated according to the following formula: EE=(Wi/Wtotal)×100%, wherein Wi is the mass of the all-trans retinoic acid in the liposome formulation which is destroyed by methanol after purification. Wtotal is the mass of the all-trans retinoic acid before dialysis and separation of free drug, which has the same volume as the all-trans retinoic acid after dialysis. The results showed that the encapsulation efficiency of ATRA loading into liposome prepared in the present embodiment was about 85.6%. Identifying according to the above method, the particle size before drug loading was 71.57 nm and the Pdl was 0.083. The particle size after drug loading was 90.25 nm and the Pdl was 0.125.

Example 9 Preparation of all-Trans Retinoic Acid Liposome with HEPES Buffer as the Internal Aqueous Phase 1. Preparation
    (1) 0.097 g of HSPC (molecular weight: 783.8), 0.031 g of DSPE-PEG2000, and 0.031 g of cholesterol were weighed and dissolved in 1.6 mL of ethanol, and water bathed to be dissolved and mixed at 70° C. in a water bath to obtain an ethanol mixture.
    (2) The obtained ethanol mixture from operation (1) was then added with 6.4 mL of 0.1 M HEPES buffer containing 10% cyclodextrin molecules, and water bathed at 70° C. for 30 minutes to obtain liposome vesicles.
    (3) The liposome vesicles obtained from operation (2) were sequentially extruded through polycarbonate membranes having 400 nm, 200 nm, 100 nm, and 50 nm pores for 8 times respectively, to finally obtain a liposome having an average particle diameter of about 90 nm.
    (4) The liposome prepared in operation (3) was dialyzed through a dialysis membrane with a 10000 MWCO in a 10% sucrose aqueous solution (pH 6~7), and the outer aqueous phase of the liposome was replaced with a 10% sucrose aqueous solution (pH 6~7), to obtain a liposome having a phospholipid bilayer membrane, and the inner aqueous phase and outer aqueous phase of the bilayer membrane have a certain concentration gradient of HPMC and HEPE.
    (5) 20 mg/mL suspension of all-trans retinoic acid was added to the liposome obtained from operation (4), the mixture was incubated for 45 minutes at 60° C. After incubation, the free all-trans retinoic acid not loading into the liposome was removed by the dialysis membrane with a 10000 MWCO, and the final all-trans retinoic acid liposome was obtained, which was labeled as Formula 8.

2. Identification of Encapsulation Efficiency of the All-trans Retinoic Acid Liposome The purified all-trans retinoic liposome formulation was destroyed with 9 volumes of methanol, and the encapsulation efficiency was determined by high performance liquid chromatography of a UV detector. Measurement conditions: ODS column (Diamonsil, 5 μm, 250×4.6 mm); detection temperature was 25° C.; detection wavelength was 340 nm; flow rate was 1.0 ml/min; mobile phase of acetonitrile/methanol (volume ratio was 95:5). The encapsulation efficiency (EE) of all-trans retinoic acid was calculated according to the following formula: EE=(Wi/Wtotal)×100%, wherein Wi is the mass of the all-trans retinoic acid in the liposome formulation which is destroyed by methanol after purification. Wtotal is the mass of the all-trans retinoic acid before dialysis and separation of free drug, which has the same volume as the all-trans retinoic acid after dialysis. The results showed that the encapsulation efficiency of ATRA loading into liposome prepared in the present embodiment was about 57.5%. Identifying according to the above method, the particle size before drug loading was 77.39 nm and the Pdl was 0.101.

The above-mentioned embodiments are just preferred embodiments of the present disclosure, and are not intended to limit the scope of the present disclosure. It should be noted that those skilled in the art can make several improvements and supplements without departing from the method of the present disclosure, which should also be considered to be within the protection scope of the present disclosure. All equivalent changes of the changes, modifications and evolutions to the above-described technical contents made by those who have common knowledge in the art without departing from the spirit and range of the present disclosure shall be still equivalent embodiments of the present disclosure; at the same time, any changes, modifications and evolutions of any equivalent changes made to the above-described embodiments in accordance with the essential art of the present disclosure are still within the scope of the technical solutions of the present disclosure.

What is claimed is:

1. An all-trans retinoic acid liposome formulation, comprising all-trans retinoic acid (ATRA) and a liposome vector comprising a lipid bilayer comprising hydrogenated soybean phosphatidyl choline (HSPC), distearoylphosphatidylethanolamine-polyethylene glycol 2000 (DSPE-PEG2000), and cholesterol (CHOL) wherein the liposome vector has an inner liposome aqueous phase comprising the ATRA, calcium acetate and water which has a pH of about 9 wherein the all-trans retinoic acid liposome formulation is prepared by an active drug loading method, that comprises the following steps:
    (1) mixing the raw materials and dissolving in ethanol to obtain an ethanol mixture;
    (2) adding an aqueous solution of calcium acetate having a pH of about 9 to the ethanol mixture in step (1) to obtain a liposome vesicle;
    (3) sequentially extruding the liposome vesicle obtained in step (2) through polycarbonate membranes having different pore diameters to obtain a blank liposome having a uniform particle diameter;
    (4) dialyzing the liposome prepared in step (3) through a dialysis membrane in an isotonic liquid having a pH of 6.0 to 7.0, to obtain a calcium acetate liposome having a pH gradient and an ion gradient between an inner aqueous phase of the calcium acetate liposome comprising the calcium acetate and an outer aqueous phase comprising the isotonic liquid; and (5) adding an all-trans retinoic acid suspension to the outer aqueous phase in step (4); and incubating and then removing free all-trans retinoic acid not encapsulated in the liposome vector, to obtain the all-trans retinoic acid liposome formulation.

2. The all-trans retinoic acid liposome formulation according to claim 1, wherein a molar ratio of the all-trans retinoic acid to the liposome vector is in a range of 1: (5-20).

3. The all-trans retinoic acid liposome formulation according to claim 1, wherein a concentration of the calcium acetate within the inner liposome aqueous phase is 120 mM to 360 mM.

4. The all-trans retinoic acid liposome formulation according to claim 1, wherein a molar ratio among HSPC, CHOL, and DSPE-PEG2000 is in a range of (30-80): (0.1-40): (0.1-30).

5. The all-trans retinoic acid liposome formulation according to claim 1, wherein the liposome vector has a particle diameter ranging from 30 nm to 200 nm.

6. The all-trans retinoic acid liposome formulation according to claim 1, wherein a concentration of the all-trans retinoic acid is 0.1 mg/ml or more.

7. An all-trans retinoic acid liposome formulation, comprising a liposome vector comprising a lipid bilayer comprising hydrogenated soybean phosphatidyl choline (HSPC), distearoylphosphatidylethanolamine-polyethylene glycol 2000 (DSPE-PEG2000), and cholesterol (CHOL), and having an inner liposome aqueous phase comprising calcium acetate and water which has a pH of about 9, and wherein the formulation further comprises an outer aqueous phase relative to the liposome vector, said outer phase comprising all-trans retinoic acid, a solubilizing molecule, and an isotonic liquid wherein the aqueous outer phase has a pH of about 6 to about 7, such that a pH gradient and an ion gradient exist between the inner and outer aqueous phases.

8. The all-trans retinoic acid liposome formulation according to claim 7, wherein the solubilizer comprises a cyclodextrin.

9. The all-trans retinoic acid liposome formulation according to claim 8, wherein the cyclodextrin comprises hydroxypropyl-β-cyclodextrin, sulfobutyl-β-cyclodextrin, or methyl=β-cyclodextrin.

10. The all-trans retinoic acid liposome formulation according to claim 1, wherein the isotonic liquid is a sucrose aqueous solution.

11. The all-trans retinoic acid liposome formulation according to claim 1, wherein the lipid bilayer consists of hydrogenated soybean phosphatidyl choline (HSPC), distearoylphosphatidylethanolamine-polyethylene glycol 2000 (DSPE-PEG2000), and cholesterol (CHOL).

* * * * *